(12) United States Patent
Matsumoto

(10) Patent No.: US 7,524,934 B2
(45) Date of Patent: Apr. 28, 2009

(54) HUMAN BRAIN CARBOXYPEPTIDASE B ANTIBODIES

(76) Inventor: Akira Matsumoto, Nishiwaki 3-5-11, Hirano-ku, Osaka-shi (JP) 547-0035

( * ) Notice: Subject to any disclaimer, the term of this patent is extended or adjusted under 35 U.S.C. 154(b) by 215 days.

(21) Appl. No.: 11/233,958

(22) Filed: Sep. 22, 2005

(65) Prior Publication Data

US 2006/0024760 A1    Feb. 2, 2006

Related U.S. Application Data

(62) Division of application No. 09/980,881, filed as application No. PCT/JP00/02878 on May 1, 2000, now Pat. No. 7,060,266.

(30) Foreign Application Priority Data

Apr. 30, 1999    (JP)    ................ 11-125169

(51) Int. Cl.
  C07K 16/00    (2006.01)
  C12N 9/00    (2006.01)
  C12Q 1/37    (2006.01)
  G01N 33/53    (2006.01)
  A61K 35/00    (2006.01)

(52) U.S. Cl. .............. 530/387.1; 435/183; 435/24; 435/7.1; 424/570

(58) Field of Classification Search ............ None
See application file for complete search history.

(56) References Cited

U.S. PATENT DOCUMENTS

| 5,206,161 | A | 4/1993 | Drayna et al. |
| 5,364,934 | A | 11/1994 | Drayna et al. |
| 5,474,901 | A | 12/1995 | Drayna et al. |
| 5,593,674 | A | 1/1997 | Drayna et al. |
| 5,985,562 | A | 11/1999 | Morser et al. |

FOREIGN PATENT DOCUMENTS

| AU | 8335098 A | 12/1998 |
| AU | 736330 B2 | 7/2001 |
| EP | 998 583 A1 | 5/2000 |
| JP | 2002-502253 T | 1/2002 |
| NO | 995914 A | 12/1999 |
| WO | WO 98/55645 A1 | 12/1998 |

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*

Eaton et al., GSP Accession No. AAR90293, "Human plasma carboxypeptidase B," Apr. 12, 1996—first entry, Mar. 25, 2003—revised.

Eaton et al., "Isolation, molecular cloning, and partial characterization of a novel carboxypepidase B from human plasma," *J. Biol. Chem.*, 266(32):21833-21838 (1991).

Fenselau et al. Sequence and expression analysis of the hrpB pathogenicity operon of *Xanthomonas campestris* pv. vasicatoria which encodes eight proteins with similarity to . . . Mol Plant Microbe Interact. Nov.-Dec. 1995; 8(6):845-54.

Goldstein et al., "Human Mast Cell Carboxypeptidase, Purification and Characterization," *J. Clin. Invest.*, 83(5):1630-1636 (1989).

Inohara et al., "Two Genes atpC1 and atpC2 for the γ Subunit of *Arabidopsis thaliana* Chlorplast ATP Synthase," *J. Biol. Chem.*, 266(12):7333-7338 (1991).

Kang et al., "The precursor of Alzheimer's disease amyloid A4 protein resembles a cell-surface receptor," *Nature*, 325(6106):733-736 (1987).

Matsumoto et al., "A human brain proteolytic activity capable of cleaving natural beta-amyloid precursor protein is affected by its substrate glycoconjugates," *Neurosci. Letters*, 242(2):109-113 (1998).

Matsumoto et al., "A Novel carboxypeptidase B that processes native β-amyloid precursor protein is present in human hippocampus," *Eur. J. Neuroscience*, 12(1)7-238 (2000).

Matsumoto et al., "Aberrant proteolysis of the beta-amyloid precursor protein in familial Alzheimer's disease lymphoblastoid cells," *Eur. J. Biochem.*, 217(1):21-27 (1993).

Matsumoto et al., "Abnormal and deficient processing of beta-amyloid precursor protein in familial Alzheimer's disease lymphoblastoid cells," *Biochem. Biophys. Res. Commun.*, 175(2):361-365 (1991).

Matsumoto et al., "Human brain carboxypeptidase B, which cleaves β-amyloid peptides in vitro, is expressed in the endoplasmic reticulum of neurons," *European J. Neuroscience*, 13(9):1653-1657 (2001).

Napier et al. Chloroplast import of the precursor of the gamma subunit of pea chloroplast ATP synthase. Plant Mol Biol. Nov. 1992; 20(4);737-41.

Reynolds et al., "Cloning and Characterization of the Novel Gene for Mast Cell Carboxypeptidase A," *J. Clin. Invest.*, 89(1):273-282 (1992).

(Continued)

*Primary Examiner*—Jeffrey Stucker
*Assistant Examiner*—Aditi Dutt
(74) *Attorney, Agent, or Firm*—Townsend and Townsend and Crew LLP

(57) ABSTRACT

A novel carboxypeptidase and the encoding gene thereof were successfully identified by screening a human hippocampus extract using brain-APP-cleaving activity as an index. Antibodies against the protein were also prepared. The antibodies are useful in, for example purifying the protein, or examining and diagnosing diseases, such as Alzheimer's disease, which cause accumulation of Aβ in the brain.

6 Claims, 10 Drawing Sheets

OTHER PUBLICATIONS

Shioi et al., "Chondroitin sulfate proteoglycan form of the Alzheimer's beta-amyloid precursor," *J. Biol. Chem.*, 267(20):13819-13822 (1992).

Tan et al., "Activation and characterization of procarboxypeptidase B from human plasma," *Biochemistry*, 34(17):5811-5816 (1995).

Yamamoto et al., "Isolation of cDNA Encoding a Human Serum Marker for Acute Pancreatitis," *J. Biol. Chem.*, 267(4):2575-2581 (1992).

Gencore OM protein - protein search, dated Sep. 19, 2002, attached to Eaton et al. reference. Attached to Restriction Requirement dated Oct. 8, 2002 in parent U.S. Appl. No. 09/980,881 (2 pages).

Sequence comparison attached to Fenselau et al. reference, dated Jan. 5, 2004 Attached to Restriction Requirement dated Mar. 10, 2004 in parent U.S. Appl. No. 09/980,881 (1 page).

Morser et al., GSN Accession No. AAV74302, "Human plasma carboxypeptidase B (PCPB) thr147 coding sequence," Apr. 28, 1999 - first entry.

N_Genseq Database Acc#ABZ48454 Nakamua et al Jun. 26, 2003. Alignment with SEQ ID No: 9.

Sequence comparison attached to Napier et al. reference, dated Jan. 5, 2004. Attached to Restriction Requirement dated Mar. 10, 2004 in parent U.S. Appl. No. 09/980,881 (1 page).

PIR_76 Database Accession No. A41204 from Eaton et al. Isolation, molecular cloning, and partial characterization of a novel carboxypeptidase B from human plasma, J. Biol. Chem. Nov. 15, 1991; 266(32):21833-8. Alignment with SEQ ID No:2.

Blast 2 Sequences results, dated Aug. 26, 2002, Submitted by facsimile in parent U.S. Appl. No. 09/980,881 (2 pages).

* cited by examiner

Figure 3

```
                                                                      agaaaattgctgttggg
  18  ATG AAG CTT TGC AGC CTT GCA GTC CTT GTA CCC ATT GTT CTC TTC TGT GAG CAG CAT GTC TTC GCG
       M   K   L   C   S   L   A   V   L   V   P   I   V   L   F   C   E   Q   H   V   F   A  22

84  TTC CAG AGT GGC CAA GTT CTA GCT GCT CTT CCT AGA ACC TCT AGG CAA GTT CAA GTT CTA CAG AAT
       F   Q   S   G   Q   V   L   A   A   L   P   R   T   S   R   Q   V   Q   V   L   Q   N  44
                                                                                           •

150  CTT ACT ACA ACA TAT GAG ATT GTT CTC TGG CAG CCG GTA ACA GCT GAC CTT ATT GTG AAG AAA AAA
       L   T   T   T   Y   E   I   V   L   W   Q   P   V   T   A   D   L   I   V   K   K   K  66

216  CAA GTC CAT TTT TTT GTA AAT GCA TCT GAT GTC GAC AAT GTG AAA GCC CAT TTA AAT GTG AGC GGA
       Q   V   H   F   F   V   N   A   S   D   V   D   N   V   K   A   H   L   N   V   S   G  88
                                           •                                       •

282  ATT CCA TGC AGT GTC TTG CTG GCA GAC GTG GAA GAT CTT ATT CAA CAG CAG ATT TCC AAC GAC ACA
       I   P   C   S   V   L   L   A   D   V   E   D   L   I   Q   Q   Q   I   S   N   D   T 110
                                                                                   •

348  GTC AGC CCC CGA GCC TCC GCA TCG TAC TAT GAA CAG TAT CAC TCA CTA AAT GAA ATC TAT TCT TGG
       V   S   P   R   A   S   A   S   Y   Y   E   Q   Y   H   S   L   N   E   I   Y   S   W 132
                      ʎ _____

414  ATA GAA TTT ATA ACT GAG AGG CAT CCT GAT ATG CTT ACA AAA ATC CAC ATT GGA TCC TCA TTT GAG
       I   E   F   I   T   E   R   H   P   D   M   L   T   K   I   H   I   G   S   S   F   E 154

480  AAG TAC CCA CTC TAT GTT TTA AAG GTT TCT GGA AAA GAA CAA ACA GCC AAA AAT GCC ATA TGG ATT
       K   Y   P   L   Y   V   L   K   V   S   G   K   E   Q   T   A   K   N   A   I   W   I 176

546  GAC TGT GGA ATC CAT GCC AGA GAA TGG ATC TCT CCT GCT TTC TGC TTG TGG TTC ATA GGC CAT AAT
       D   C   G   I  (H)  A  [R] (E)  W   I   S   P   A   F   C   L   W   F   I   G   H   N 198

612  CGA ATG TGG AGA AAG AAC CGT TCT TTC TAT GCG AAC AAT CAT TGC ATC GGA ACA GAC CTG AAT AGC
       R   M   W   R   K  [N] [R]  S   F   Y   A   N   N   H   C   I   G   T   D   L   N  [R]220

678  AAC TTT GTC TCC AAA CAC TGG TGT GAG GAA GGT GCA TCC AGT CCT CA TGC TCG GAA ACC TAC TGT
       N   F   A   S   K   H   W   C   E   E   G   A   S   S   S   S   C   S   E   T   Y   C 242

744  GGA CTT TAT CCT GAG TCA GAA CCA GAA GTG AAG GCA GTG GCT AGT TTC TTG AGA AGA AAT ATC AAC
       G   L   Y   P   E   S   E   P   E   V   K   A   V   A   S   F   L   R   R   N   I   N 264

810  CAG ATT AAA GCA TAC ATC AGC ATG CAT TCA TAC TCC CAG CAT ATA GTG TTT CCA TAT TCC TAT ACA
       Q   I   K   A   Y   I   S   M  (H) [S] [Y]  S   Q   H   I   V   F   P   Y   S   Y   T 286

876  CGA AGT AAA AGC AAA GAC CAT GAG GAA CTG TCT CTA GTA GCC AGT GAA GCA GTT CGT GCT ATT GAC
       R   S   K   S   K   D   H   E   E   L   S   L   V   A   S   E   A   V   R   A   I   E 308

942  AAA ACT AGT AAA AAT ACC AGG TAT ACA CAT GGC CAT GGC TCA GAA ACC TTA TAC CTA GCT CCT GGA
       K   T   S   K   N   T   R   Y   T   H   G   H   G   S   E   T   L  [Y]  L   A   P   G 330

1008  GGT GGG GAC GAT TGG ATC TAT GAT TTG GGC ATC AAA TAT TCG TTT ACA TCA AAC CCA CCT GTA GAG
       G   G  [D]  D   W   I   Y   D   L   G   I   K   Y   S   F   T   S   N   P   P   V   E 352

1074  AAG CTT TTG CCG CTG TCT CTA AAA TAG cttggcatgtcattaggaatgtttaatgcccctgatttatcattctgctt
       K   L   L   P   L   S   L   K   =                                                   360

1152  ccgtattttaatttactgattccagcaagaccaaatcattgtatcagattattttaagtttatccgtagttttgataaaagattt 1239  tcctattccttggttctgtcagagaacctaataagtgctactttgccattaaggcagactagggttcatgtcttttacccttaaa 1326  aaaaaattgtaaaagtctagttacctacttttctttgatttcgacgtttgactagccatctcaagcaactttcgacgtttgacta 1413  gccatctcaagcaagtttaatcaaagatcatctcacgctgatcattggatcctactcaacaaaaggaagggtggtcagaagtacatt 1500  aaagatttctgctccaaatttcaataaatttcttcttctccttaaaaaaaaaaaaaaaaaaaaaaaaaaaaa
```

Figure 4
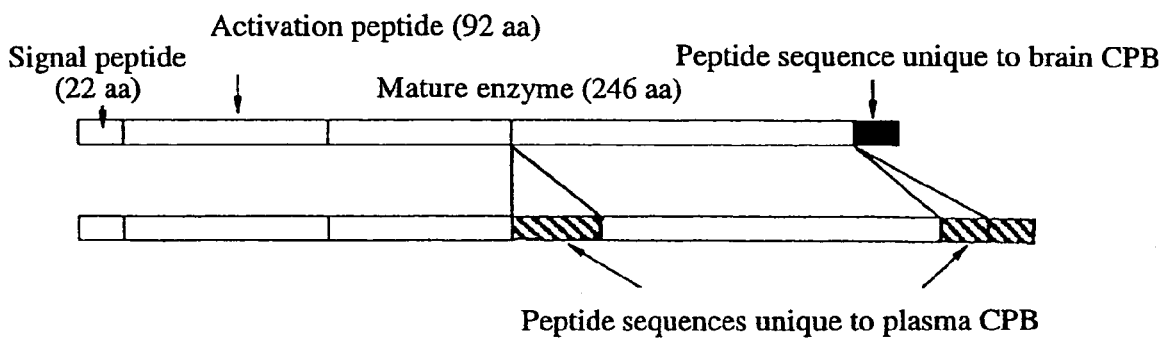
B
```
HBCPB2(347-360)   S N P  P V E K  L L P L S  L K - C-terminus
atpSr(181-194)    S N P  T I G T  L L P L S  P M
atpSo(182-195)    S D P  V I H T  L L P L S  P K
atpC1(182-195)    S E P  V I H T  L L P L S  P K
atpC2(183-196)    S D P  V I H T  L L P L S  P K
```
C
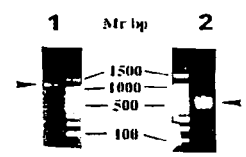

Figure 6
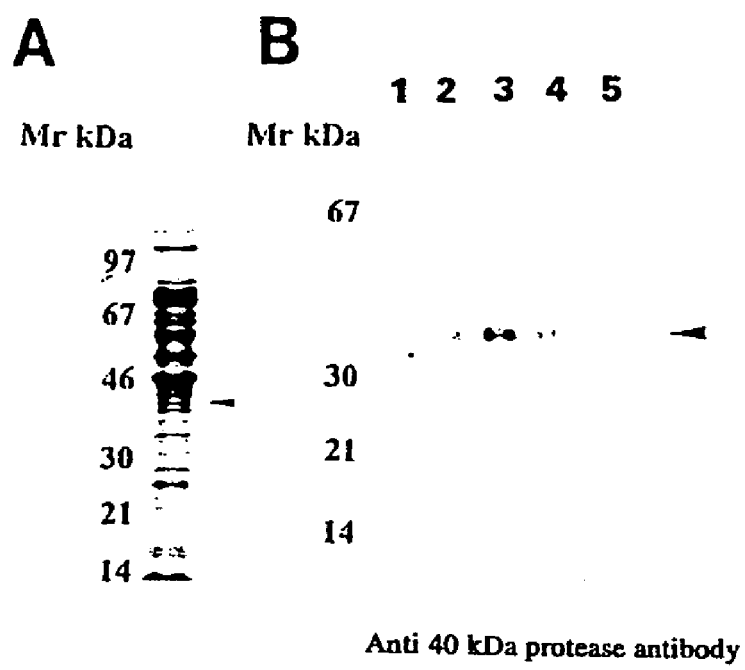
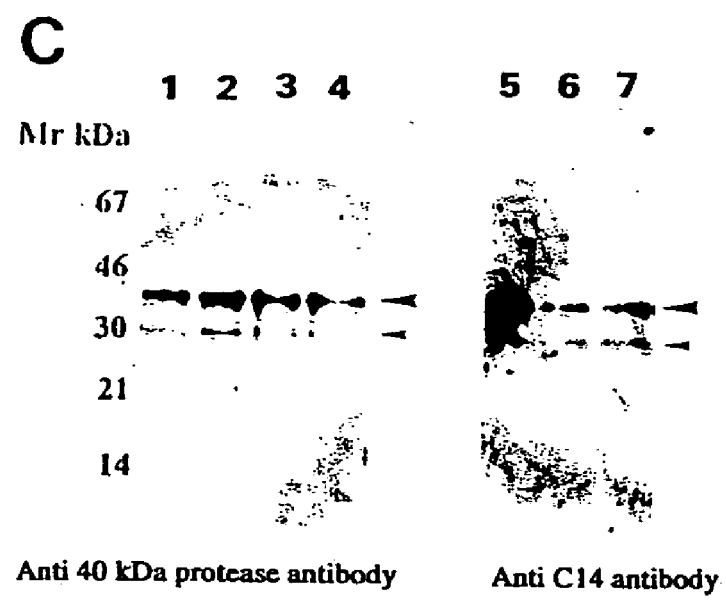

Figure 10
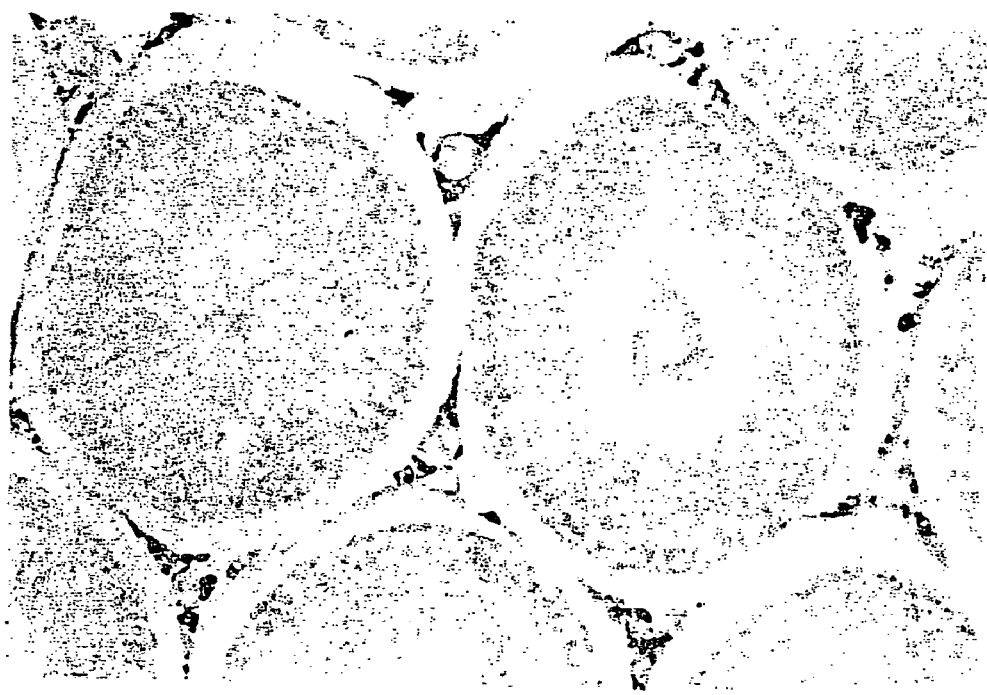
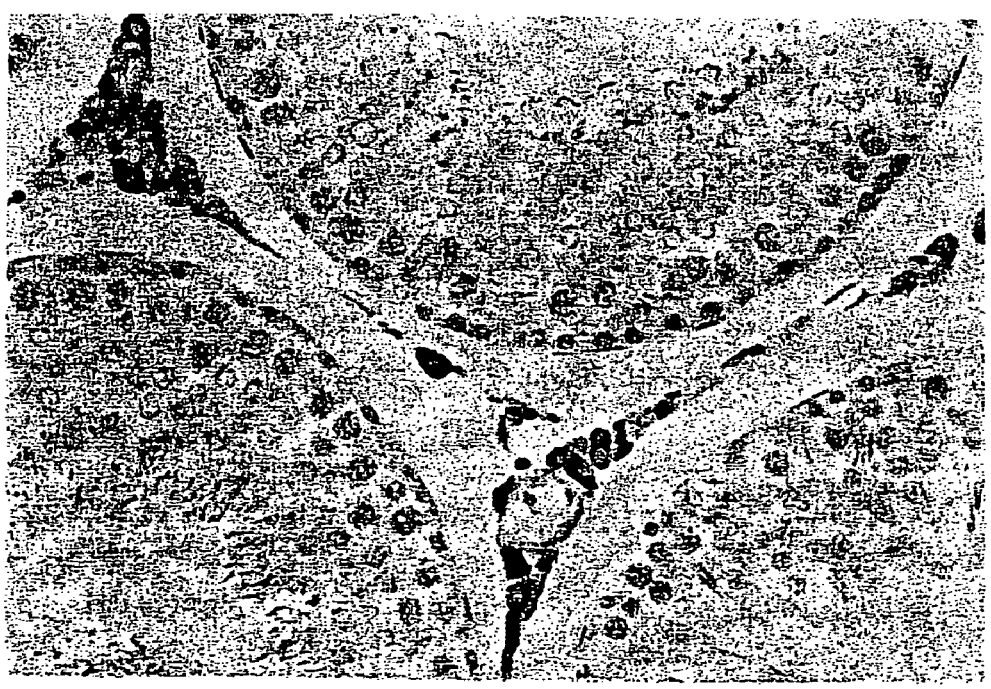

HUMAN BRAIN CARBOXYPEPTIDASE B ANTIBODIES

CROSS REFERENCE TO RELATED APPLICATIONS

This application is a divisional application of U.S. patent application Ser. No. 09/980,881, filed Mar. 28, 2002, now U.S. Pat. No. 7,060,266, which is a U.S. 371 national stage application of International Application No. PCT/JP00/02878, filed May 1, 2000, now WO 00/66717, published Sep. 11, 2000, which claims the benefit of priority to Japanese patent application 11/125,169, filed Apr. 30, 1999, the disclosures of which are all incorporated herein by reference.

TECHNICAL FIELD

The present invention relates to a novel carboxypeptidase, and the gene, a method of production, and uses thereof.

BACKGROUND ART

Alzheimer's disease (AD) is a neurodegenerative disorder in the brain cortex, and progressive loss of neurons along with the progression of the disease eventually results in dementia. Major neuropathological findings are brain atrophy, senile plaques, neurofibrillary tangles and amyloid angiopathy. In both AD and normal brain aging, neuronal loss and abnormal deposition of Aβ, a major, essential constituent in senile plaques and cerebrovascular amyloid, appear in a topologically unique fashion, these lesions predominating in particular areas of the cerebral cortex, such as the hippocampus and enthorhinal cortex, which participate in memory and recognition. Mounting evidence suggests that missense mutations in and around Aβ are responsible for several types of familial AD and related disorders (Chartier-Harlin, M.-C. et al., 1991, Nature 353: 844-846; Haass, C. et al., 1995, Nature Med. 1: 1291-1296; Van Broeckhoven, C. et al., 1990, Science 248: 1120-1122). Two causative genes for another type of familial AD were identified as encoding presenilin 1 and 2, similar transmembrane proteins presumably expressed in the endoplasmic reticulum and/or Golgi complex (Sherrington, R. et al., 1995, Nature 375: 754-760; Levy-Lehad, E. et al., 1995, Science 269: 970-977). These proteins may participate in the modification and processing of newly synthesized proteins including β-amyloid precursor protein (APP). Of the Aβ peptides found in the brain, Aβ1-42 is highly amyloidogenic and an increase of this within neuronal cells may be directly associated with the pathophysiology of AD (Hardy, J., 1995, Trends. Neurosci. 20: 154-159; Beyreuther, K. and Masters, C. L., 1997, Nature 389: 677-678; Younkin, S. G., 1995, Ann. Neurol. 37: 287-288). Recently, distinctive neuronal sites for the intracellular production of Aβ have been identified as the endoplasmic reticulum for Aβ1-42 and the trans-Golgi network for Aβ1-40 (Hartmann, T. et al., 1997, Nature Med. 3: 1016-1020; Cook, D. G. et al., 1997, Nature Med. 3: 1021-1023). These findings strongly suggest that any impairment in the modification, processing or trafficking of APP and the Aβ peptides is essentially linked to the pathophysiology of AD. Although the causative genes and proteins have been identified in rare familial AD cases, the majority of AD cases (more than 95%) are sporadic, and the genes or proteins responsible for the disease process have yet to be identified. Whatever the primary pathogenesis of individual AD cases, progression of AD results in the accumulation and aggregation of Aβ in the brain, which eventually may induce neuronal death possibly through $Ca^{2+}$ ion-channel formation, free radical generation by microglia and/or an apoptotic mechanism (Loo, D. T. et al., 1993, Proc. Natl. Acad. Sci. USA 90: 7951-7955; Arispe, N. et al., 1993, Proc. Natl. Acad. Sci. USA 90: 567-571).

The proteolytic process that generates Aβ species has yet to be clarified. Although candidate proteases that have α, β or γ-secretase activity have been identified from various species and organs, the majority of them were prepared by assays of their activities with synthetic substrates, and only a few of these candidate proteases have activity for the natural APP substrate. Induction of any of the identified genes responsible for familial AD in transgenic mice failed to show the neuropathological findings detected in human brain. Recent findings for monkey brain microinjected with fibrillary Aβ suggest that the neurotoxicity of Aβ in vivo is a pathological reaction of the aged brain, predominantly in the higher primates (Geula, C. et al., 1998, Nature Med. 4: 827-831) These findings suggest that Aβ and Aβ-bearing peptides are generated in a species- and tissue-specific manner, but the molecular mechanism is unclear.

DISCLOSURE OF THE INVENTION

An objective of the present invention is to provide a novel carboxypeptidase expressed in brain and comprising a peptidase activity for brain APP, and the gene, a method of production, and uses thereof.

The present inventors previously analyzed the processing of APP and Aβ-containing peptides in lymphoblastoid cells derived from patients with familial AD (Matsumoto, A. and Fujiwara, Y., 1993, Eur. J. Biochem. 217: 21-27; Matsumoto, A. and Matsumoto, R., 1994, Eur. J. Biochem. 225: 1055-1062). In the culture media of familial AD cells, the inventors found a 68 kDa serine protease that shows β-secretase-like activity for synthetic substrates (Matsumoto, A. and Fujiwara, Y., 1994, Biochemistry 33: 3941-3948). This protease also cleaves natural APP prepared from lymphoblastoid cells (LAPP) and its Aβ-containing fragment at a site(s) in the vicinity of the Aβ-N-terminus (Matsumoto, A. et al., 1995, Neurosci. Lett. 195:171-174). This serine protease, however, does not degrade natural brain APP as revealed by measuring this protease's activity using natural brain APP prepared from normal human brain as the substrate. Therefore, the inventors thought that natural APP as a substrate has tissue-specificity, and that it should be possible to identify a novel protease that uses natural brain APP as the substrate by screening proteases expressed in brains using natural brain APP-cleaving activity as an index.

The present inventors searched for protease activity towards natural brain APP in the homogenate fractions of the human hippocampus, and by analyzing the active fractions, succeeded in separating a 40-kDa protein that has the activity to produce Aβ-containing peptide by cleaving brain APP at multiple sites. Analysis of this protein revealed that it was a novel protease belonging to the carboxypeptidase (CP) family. This protease (brain carboxypeptidase B; brain CPB) is not an alternatively spliced isoform of plasma CPB, rather it has such specific features as 14 C-terminal amino acids. Northern analysis using a human brain CPB-cDNA probe and Western analysis using a human brain CPB-specific antibody detected a brain-specific expression of this protease. An immunohistochemical study showed that the protease is expressed in neuronal perikarya, particularly in that of the pyramidal neurons of the hippocampus, ependymal-choroid plexus cells, and in a portion of the microglia of normal brains. This protease existed in spinal fluid and blood a little. In brains of patients with sporadic AD, decreased neuronal expression and a cluster of microglia with protease immunoreactivity associated with its extracellular deposition being detected. Furthermore, Western analysis using anti-Aβ N terminus antibody proved that human brain CPB has exopeptidase activity in which the Aβ peptide is digested from its C-terminal end.

These findings suggest that brain CPB isolated by the inventors has a physiological function in APP processing and may have significance in AD pathophysiology. Therefore, brain CPB itself, isolated by the present inventors, could be used as a drug for preventing and treating Alzheimer's disease, and for screening drugs for prevention and treatment. Furthermore, brain CPB isolated by the inventors may be used in tests for Alzheimer's disease.

In addition, brain CPB isolated by the present inventors, and compounds that may regulate its activity, may be applied not only for the Alzheimer's disease mentioned above, but also for the prevention, treatment, and diagnosis of various other diseases causing accumulation of Aβ.

Therefore, the present invention provides:

(1) a protein comprising the amino acid sequence of any one of SEQ ID NOs: 2 to 4,
(2) a protein comprising peptidase activity towards brain APP, wherein said protein is selected from,
(a) a protein comprising an amino acid sequence in which one or more amino acids are replaced, deleted, inserted, and/or added to the amino acid sequence of any one of SEQ ID NOs: 2 to 4,
(b) a protein encoded by a DNA that hybridizes with a DNA comprising the nucleotide sequence of SEQ ID NO: 1,
(3) a DNA encoding the protein of (1) or (2),
(4) the DNA of (3) comprising the coding region of the nucleotide sequence of SEQ ID NO: 1,
(5) a vector into which the DNA of (3) or (4) is inserted,
(6) a host cell carrying the vector of (5),
(7) a method for producing the protein of (1) or (2), wherein said method comprises the steps of culturing the host cell of (6), and collecting from the cell or its culture supernatant, a recombinant protein expressed within the cell,
(8) an antibody against the protein of (1) or (2),
(9) a partial peptide of the protein of (1) or (2),
(10) a polynucleotide comprising at least 15 nucleotides, which hybridizes with a DNA comprising the nucleotide sequence of SEQ ID NO: 1 or its complementary strand,
(11) a method for screening a compound that binds to the protein of (1) or (2), comprising the steps of:
(a) contacting a test sample with the protein or a partial peptide thereof,
(b) detecting the binding activity between the test sample and the protein or the partial peptide thereof, and
(c) selecting a compound that has an activity to bind to the protein or the partial peptide thereof,
(12) a compound that binds to the protein of (1) or (2), (13) the compound of (12), wherein said compound is isolated by the method of (11),
(14) a method for screening a compound that promotes or inhibits the peptidase activity of the protein of (1) or (2), comprising the steps of:
(a) contacting the protein of (1) or (2) with its substrate in the presence of a test sample,
(b) detecting the cleavage of the substrate, and
(c) selecting a compound comprising the activity to increase or decrease substrate cleavage caused by the protein of (1) or (2), in comparison to the cleavage in the absence of the test sample (control)
(15) the method of (14), wherein said substrate is brain APP,
(16) a compound comprising the activity to promote or inhibit peptidase activity of the protein of (1) or (2),
(17) the compound of (16), wherein said compound is isolated by the method of (14) or (15),
(18) an Aβ production regulator, comprising the protein of (1) or (2) as an active ingredient,
(19) a drug for treating a disease that causes accumulation of Aβ in the brain, wherein said drug comprises the protein of (1) or (2) as an active ingredient,
(20) the drug of (19), wherein said disease that causes accumulation of Aβ in the brain is selected from the group consisting of senile dementia, Alzheimer's disease, Down's syndrome, hereditary cerebral hemorrhage, and cephalic contusion,
(21) an Aβ production regulator, comprising a compound of any one of (12), (13), (16), or (17) as an active ingredient,
(22) a drug for treating a disease that causes accumulation of Aβ in the brain, comprising a compound of any one of (12), (13), (16), or (17) as an active ingredient,
(23) the drug of (22), wherein said disease that causes accumulation of Aβ in the brain is selected from the group consisting of senile dementia, Alzheimer's disease, Down's syndrome, hereditary cerebral hemorrhage, and cephalic contusion,
(24) a kit for screening a compound that promotes or inhibits peptidase activity of the protein of (1) or (2), wherein said kit comprises the protein of (1) or (2),
(25) the kit of (24), further comprising a substrate of the protein of (1) or (2),
(26) the method of (25), wherein said substrate is brain APP,
(27) a method for testing a disease that causes accumulation of Aβ in the brain, comprising the steps of:
(a) preparing a sample from a subject, and
(b) detecting the amount of the protein of (1) or (2) contained within the sample, using the antibody of (8),
(28) the method of (27), wherein said sample is spinal fluid or serum,
(29) the method of (27) or (28), wherein said disease that causes accumulation of Aβ in the brain is selected from the group consisting of senile dementia, Alzheimer's disease, Down's syndrome, hereditary cerebral hemorrhage, and cephalic contusion,
(30) a reagent for testing a disease that causes accumulation of Aβ in the brain, comprising the antibody of (8), and
(31) the reagent of (30), wherein said disease that causes accumulation of Aβ in the brain is selected from the group consisting of senile dementia, Alzheimer's disease, Down's syndrome, hereditary cerebral hemorrhage, and cephalic contusion.

The present invention relates to a novel brain carboxypeptidase B (brain CPB) protein expressed in the brain, which has peptidase activity towards brain APP. Human brain CPB protein included in the protein of this invention was isolated from an extract of human hippocampus using decomposition activity towards brain APP as an index. In addition, the gene encoding human brain CPB protein was cloned by immunological screening using antibodies against human brain CPB protein and by RT-PCR and RACE using a primer that was synthesized based on the partial amino acid sequence of human brain CPB protein. SEQ ID NO: 1 shows the nucleotide sequence of a cDNA encoding the human brain CPB isolated by the present inventors, and SEQ ID NO: 2 shows the amino acid sequence of human brain CPB protein (pre-pro-form) encoded by this cDNA. The human brain CPB of this invention is thought to be initially synthesized as a pre-proprotein, then a signal sequence is removed by cleavage to produce the proprotein, furthermore the activation peptide is removed by cleavage to produce the mature protein. SEQ ID NO: 3 shows the amino acid sequence of the pro-protein of human brain CPB of this invention, and SEQ ID NO: 4 shows the amino acid sequence of the mature protein. In the present invention, "brain APP" refers to APP molecular species expressed in the brain. Examples of molecular species of human brain APP are APP695 (Kang, J. et al. (1987) Nature 325, 733-736) and Appican (Shioi, J. et al. (1992) J. Biol. Chem. 267, 13819-13822), but are not limited to these examples.

Human brain CPB has the activity to produce Aβ-containing peptides by cleaving APP, prepared from the human brain, at multiple sites. It is thought that the human brain. CPB is synthesized as a 40-kDa preproprotein, and therefrom, a 30-kDa mature protein is produced. From the characteristics of the amino acid sequence, this protein was determined to be a novel protease belonging to the CPB family (brain carboxypeptidase B; brain CPB). This protease has high homology to a known human plasma CPB (HPCPB) belonging to the CPB family, but since it has specific characteristics, such as a unique set of 14 amino acids at its C terminus, this was presumed to be an independent gene, and not an isoform produced by alternative splicing of plasma CPB.

Among human organs examined by Northern analysis, human brain CPB (HBCPB) was found only in the brain. Antibody against C-terminal 14 amino acids of HBCPB (anti C14 antibody) showed signals in the neuronal perikaryon and a portion of the microglia (FIG. 7), but not in the liver in which HPCPB is synthesized. Furthermore, in the RT-PCR analysis of brain mRNAs, only a 1077 bp band that is unique to a processed form of prepro-HBCPB was detected (FIG. 4C). Moreover, immunological screening done with anti prepro-HBCPB antibody gave three cDNA clones that had almost identical restriction enzyme patterns, indicating that HBCPB is the only CPB isoform expressed in human brain.

Immunohistochemical analysis for normal brains indicates that HBCPB is expressed in various neuronal perikaria, particularly in that of the pyramidal neurons of the hippocampus, ependymal cells, choroid plexus cells, and in a portion of the microglia, but not in astrocytes. In AD brains, HBCPB seems to be expressed in a portion of the clustered microglia as parenchymal deposits with or without glial infiltration. Furthermore, in senile plaques from five AD brains, there was partial colocalization of the protease immunoreactivity, ranging from 10% to 60% of all the plaques in each brain. Moreover, in parenchyma of the hippocampus, round homogeneous deposits with HBCPB- and C14-immunoreactivities were common to all five AD brains, which differ markedly from amyloid bodies (FIG. 9G). Enhanced infiltration of microglia is a common finding in aged and AD brains. The significance of the microglia in relation to senile plaque formation is not clear. Wisniewski et al. (Wisniewski, H. M. et al., 1989, Can. J. Neurol. Sci. 16: 535-542) reported Aβ fibrils in the endoplasmic reticulum of activated microglia in the immediate vicinity of Aβ deposits, suggesting that activated microglia may synthesize as well as process Aβ-peptides. APP isoforms in the microglia, which are mesodermal in origin, have LAPP, and APP with the Kunitz protease inhibitor domain, neither of which are expressed neurons. Another hypothesis is that the microglia are not involved in initial plaque formation, rather they process Aβ peptides through phagocytosis (Frackowiak, J. et al., 1992, Acta Neuropathol. 84: 225-233). Choroid plexus cells secrete cerebrospinal fluid (CSF) and ependymal cells are speculated to have secretion, absorption and transport functions and to provide a barrier between the brain and CSF (Del Bigio, M. R., 1995, Glia 14: 1-13). The expression of anti C14 immunoreactivity in these cells suggests that HBCPB is necessary for processing the peptides synthesized in brain cells, including the appropriate isoform of APP. Under physiological conditions, target substrates in the neurons appear to have at least two chances to come across the protease, in the perikaria and in ependymal cells before it is released into the CSF. In AD, the presence of HBCPB in the extracellular space associated with enhanced activation of the microglia may represent a pathophysiological condition.

In addition, experiments confirmed that Aβ peptide is a substrate of the human brain CPB.

From the above-mentioned findings, the brain CPB protein of this invention is thought to be deeply involved with the onset of Alzheimer's disease and with the production of Aβ formed by decomposition of brain APP.

That is, the loss of balance the functions of proteases including the brain CPB protein of this invention, appears to be causing the abnormal accumulation of Aβ.

The human brain CPB of this invention may have the function of reducing nerve cell death by decreasing and metabolizing the highly self-aggregating β-amyloid peptides (especially β-amyloid 1-42) accumulating in the brain.

Besides, its use as a subject for research to elucidate the molecular mechanism of Aβ production, the brain CPB protein of this invention itself can be used as a drug. For example, it could be possible to improve Aβ metabolism by continuously infusing the protein of this invention into the cerebrospinal fluid of an AD patient to elevate the concentration of human brain CPB in the cerebrospinal fluid, and thus promoting the uptake of the protein into nerve cells via ependymal cells to supplement the decreased or depleted human brain CPB.

In addition, the brain CPB of this invention can be used as a tool for screening promoters or inhibitors of the protein of this invention useful as a drug. Furthermore, the protein of this invention or a compound that regulates the activity of the protein of this invention is useful as a drug for preventing or treating various diseases that involve pathological conditions of accumulation of Aβ peptide in the brain, and as an agent for testing and diagnosing such diseases. Examples of such diseases are senile dementia, Alzheimer's disease, Down's syndrome, hereditary cerebral hemorrhage (Holland type, etc.), and cephalic contusion (boxer's brain), and such.

As long as there is a peptidase activity towards brain APP, the present invention includes proteins that are structurally similar to the natural human brain CPB protein (SEQ ID NOs: 2, 3, and 4). Such structurally similar proteins include mutants of natural human brain CPB protein, and brain CPB proteins derived from other organisms.

One skilled in the art would readily prepare these proteins using, for example, standard mutagenesis methods. Known methods for altering amino acids in proteins include Kunkel's method (Kunkel, T. A. (1985) Proc. Natl. Acad. Sci. USA 82, 488; Kunkel, T. A. et al. (1987) Methods in Enzymology 154, 367), Gapped duplex method (Kramer, W. et al. (1984) Nucl. Acids. Res. 12, 9441; Kramer, W. et al. (1987) Methods in Enzymology 154, 350), Oligonucleotide-directed Dual Amber (ODA) method (Hashimoto-Gotoh, T. et al. (1995) Gene 152, 271-275; Zoller, M. J. and Smith, M. (1983) Methods in Enzymology 100, 468), etc. In artificial alteration of amino acids in proteins, the number of amino acid residues to be altered is usually 30 or less, preferably 10 or less, and more preferably 5 or less. Alteration of amino acids in proteins could occur spontaneously. Such proteins having amino acid sequences different from that of the natural human brain CPB protein (SEQ ID NOs: 2, 3, and 4) due to artificial or spontaneous substitution, deletion, addition and/or insertion of amino acid residues, are also included in this invention as long as they have a peptidase activity to brain APP.

An amino acid having properties similar to those of the amino acid to be substituted is preferably used for substitution. Since Ala, Val, Leu, Ile, Pro, Met, Phe and Trp are, for example, all classified into the non-polar amino acid, they are considered to have similar properties. Non-charged amino acids include Gly, Ser, Thr, Cys, Tyr, Asn, and Gln. Acidic amino acids include Asp and Glu, while basic amino acids include Lys, Arg and His.

Proteins structurally similar to the human brain CPB protein having a peptidase activity against brain APP can be prepared using the known hybridization technique (2.9 Southern Blotting and Hybridization 2.9.1-2.9.10 (Selden, R. F.), 4.9 Analysis of RNA by Northern Hybridization 4.9.1-4.9.8 (Selden, R. F.), 6.3 Hybridization with Radioactive Probes Using DNA Fragments 6.3.1-6.3.6 (Straus, W. M.), 6.4 Hybridization with Radioactive Probes Using Oligonucleotides 6.4.1-6.4.5 (Duby, A.), in 'Current Protocols in Molecular Biology' (Ausubel, F. M., Brent, R., Kingston, R. E., Moore, D. D., Seidman, J. G., Smith, J. A., Struhl, K. eds.) John Wiley & Sons, New York (1987)) and polymerase chain reaction (PCR) technique (Optimization of PCRs 3-12 (Innis, M. A. and Gelfand, D. H.), Amplification of Genomic DNA 13-20 (Saiki, R. K.), Amplification of RNA 21-27 (Kawasaki, E. S.), RACE: Rapid Amplification of cDNA Ends 28-38 (Frohman, M. A.), Degenerate Primers for DNA Amplification 39-45 (Compton, T), cDNA Cloning Using Degenerate Primers 46-53 (Lee, C. C. and Caskey, T.), in 'PCR Protocols' (Innis, M. A., Gelfand, D. H., Sninsky, J. J., White, T. J. eds.) Academic Press, San Diego (1990)). It is routine for one skilled in the art to isolate DNA highly homologous to human brain CPB cDNA from various other organisms using the human brain CPB cDNA (SEQ ID NO: 1) or portions thereof as a probe and oligonucleotides specifically hybridizing with the human brain CPB cDNA (SEQ ID NO: 1) as a primer to obtain proteins structurally similar to the human brain CPB protein from the isolated DNA.

Proteins encoded by DNAs hybridizing with the human brain CPB cDNA are included in this invention as long as they have a peptidase activity against brain APP. Other organisms used for isolating such proteins include, for example, monkeys, mice, rats, rabbits, goats, cattle, sheep, pigs, dogs, and so on, but are not limited thereto. cDNAs encoding such proteins can be isolated from such sources as brains of these organisms, for example, hippocampus.

DNAs encoding the brain CPB protein derived from organisms other than human are usually highly homologous to human brain CPB. Being highly homologous means at least 40% or more, preferably 55% or more, and further preferably 70% or more (e.g. 85% or more, 90% or more, 95% or more) sequence identity at the amino acid level. Sequence homology can be determined by the homology search program of Data Bank of Japan: DDBJ (National Institute of Genetics), such as FASTA, BLAST, etc.

One skilled in the art can readily determine conditions for hybridization to isolate DNAs encoding proteins functionally equivalent to the human brain CPB protein. One example of hybridization conditions when the DNAs are isolated from a brain cDNA library using $^{32}$P-labeled probe is as follows. After hybridization, washing is done under the low stringent conditions of 55° C., 2×SSC, and 0.1% SDS, more preferably, moderately stringent conditions of 55° C., 0.2×SSC, and 0.1% SDS, and still more preferably, highly stringent conditions of 68° C., 0.2×SSC, and 0.1% SDS. In this case, although plural factors including the temperature, salt concentration, and such are thought to influence the stringency of hybridization, one skilled in the art would readily determine the stringent conditions similar to above by suitably selecting these factors. When the cDNAs are isolated from other tissues, washing is preferably done under high stringent conditions since similar CPBs may be expressed therein.

The protein of this invention can be prepared as either a natural protein or a recombinant protein utilizing gene recombination techniques. Natural proteins can be prepared by, for example, subjecting extracts from tissues that are supposed to contain the brain CPB protein (for example, hippocampus) to affinity chromatography using the antibody to the brain CPB protein as described below. In addition, as indicated in the Examples, a natural protein can be prepared by collecting the fraction that bound to a benzamidine-Sepharose column, and by appropriately combining preparative PAGE, etc. On the other hand, recombinant proteins may be prepared by culturing cells transformed with DNA encoding the brain CPB protein, allowing the transformants to express the protein, and recovering the protein as described below.

The invention also includes partial peptides of the proteins of this invention. An example of partial peptides of the proteins of this invention may be a peptide containing the boundary portion of the activation peptide and the mature protein, among the proteins of this invention. Such a peptide is thought to act antagonistically in the production of the mature form of the protein of this invention by acting on the protease mediating the reaction that cleaves the mature protein from the proprotein In addition, an example of the partial peptides of the proteins of this invention may be a peptide that corresponds to the substrate-binding site of the protein of this invention. This type of partial peptide may be utilized as inhibitors, and such, of the protein of this invention by biological administration. These partial peptides are useful as an inhibitor or activator of signal transduction that is mediated by the protein of this invention. Additionally, examples of the partial peptides of this invention may be a partial peptide of the C-terminal region of the protein of this invention (for example, SEQ ID NOs: 2, 3, and 4), and this peptide may be utilized to prepare an antibody. In addition, as the partial peptides of the proteins of this invention, an activation peptide may be cited. Partial polypeptides comprising the amino acid sequence specific to the protein of this invention have at least 7, preferably at least 8, more preferably at least 9 amino acid residues. Partial peptides of this invention can be produced by, for example, genetic engineering techniques, known peptide synthetic methods, or by digestion of the protein of this invention with appropriate peptidases.

This invention also relates to DNAs encoding the proteins of the invention. DNAs encoding the protein of this invention are not particularly limited as long as they can encode the proteins of this invention, including cDNAs, genomic DNAs, and synthetic DNAs. DNAs having any desired nucleotide sequences based on the degeneracy of genetic codes are also included in this invention as long as they can encode the proteins of this invention.

cDNAs encoding the proteins of this invention can be screened, for example, by labeling cDNA of SEQ ID NO: 1 or segments thereof, RNAs complementary to them, or synthetic oligonucleotides comprising partial sequences of said cDNA with $^{32}$P, etc., and hybridizing them with a cDNA library derived from tissues (e.g., hippocampus, etc.) expressing the proteins of this invention. Such cDNAs can be cloned by synthesizing oligonucleotides corresponding to nucleotide sequences of these cDNAs, and amplifying them by PCR with cDNA derived from suitable tissues (e.g. hippocampus, etc.) as a template. The genomic DNA can be screened, for example, by labeling cDNA of SEQ ID NO: 1 or segments thereof, RNAs complementary to them, or synthetic oligonucleotides comprising partial sequences of said cDNA with $^{32}$P, etc., and hybridizing them with a genomic DNA library. Alternatively, the genomic DNA can be cloned by synthesizing oligonucleotides corresponding to nucleotide sequences of these cDNAs, and amplifying them by PCR with genomic DNA as a template. Synthetic DNAs can be prepared, for example, by chemically synthesizing oligonucleotides comprising partial sequences of cDNA of SEQ ID NO: 1, annealing them to form double strand, and ligating them with DNA ligase.

These DNAs are useful for the production of recombinant proteins. The proteins of this invention can be prepared as recombinant proteins by inserting DNAs encoding the proteins of this invention (e.g. DNA of SEQ ID NO: 1) into an appropriate expression vector, transforming suitable cells with the vector, culturing the transformants, and purifying expressed proteins from the transformants or culture supernatant of them.

For example, when expressing a recombinant protein using *E. coli* as the host, examples of systems that can be used are: the pET System (Novagen) that allows induction of expression by T7 RNA polymerase and attachment of various tags; the pET CBD Fusion System 34b-38b (Novagen) that allows expression of the protein of this invention as a fusion protein with the cellulose binding domain followed by purification by affinity chromatography using a cellulose carrier; and, the GST Gene Fusion System (Pharmacia) that allows expression of the protein of this invention as a fusion protein with glutathione S-transferase followed by purification by glutathione Sepharose 4B. In addition, there is no limitation on the host used to express the proteins of this invention, and it is possible to use a known vector system for expression in yeast, insect cells, mammalian cells, and such. For the purpose of expression in neurons, a system using Semliki Forest Virus (SFV) vector (Tienari, P. J. et al., EMBO J. 15: 5218-5229 (1996), etc.) may be used, for example.

Recombinant proteins expressed in host cells can be purified by known methods. The protein of this invention expressed in the form of a fusion protein, for example, with a histidine residue tag or glutathione-S-transferase (GST) attached at the N-terminus can be purified by a nickel column or a glutathione sepharose column, etc. In addition, when the protein of the present invention is expressed as a fusion protein, the portion comprising the protein of this invention can be recovered by inserting cleavage sites, such as Thrombin and Factor Xa, into the boundary area.

The DNA encoding the protein of this invention or its antisense DNA, and such, may also be utilized for gene therapy of diseases caused by abnormalities in the protein of this invention (abnormalities in expression and function). There is no limitation on the vector to be used for gene therapy, as long as a therapeutically effective expression can be achieved by the vector, and examples of vectors are adenovirus vectors, Semliki Forest virus vectors, and such (Chen, J. et al. (1998) Cancer Res. 58, 3504-3507; Barkats, M. et al. (1998) Progress in Neurobiology 55, 333-341).

For example, gene-therapy can be carried out after producing a vector in which prepro-human brain CPB-cDNA has been inserted by matching the frame with a Semliki Forest virus vector (pSFV-1), completing the genetically recombined virus using a helper virus, then selecting a patient appropriate for treatment by analyzing the general condition of the patient and virus antibody value, and conducting gene therapy on this patient.

The present invention also relates to polynucleotides hybridizing with the DNA comprising the nucleotide sequence of SEQ ID NO: 1 or its complementary sequence, and containing at least 15 nucleotides. Preferably, the polynucleotides specifically hybridize with the DNA comprising the nucleotide sequence of SEQ ID NO: 1 or its complementary sequence. "Specifically hybridize" means that a polynucleotide does not significantly cross-hybridize with DNAs encoding other proteins under usual hybridization conditions, preferably under stringent hybridization conditions as described above. Such polynucleotides include probes, primers, nucleotides or nucleotide derivatives (e.g. antisense oligonucleotides and ribozymes, etc.), which can specifically hybridize with DNAs encoding the proteins of this invention, or DNAs complementary to said DNAs.

cDNAs encoding the proteins of this invention or oligonucleotides comprising partial sequences thereof can be used for cloning genes and cDNAs encoding the proteins of this invention, or amplifying them by PCR. The cDNAs and oligonucleotides can also be utilized for detecting polymorphism or abnormality (gene diagnosis, etc.) of the gene or cDNA by the restriction fragment length polymorphism (RFLP) method, single strand DNA conformation polymorphism (SSCP) method, etc.

This invention also relates to antibodies binding to the proteins of the invention. The antibodies against the proteins of this invention can be prepared by known method (Scheidtmann, K. H., Immunological detection of known sequence, in "Protein structure", T. E. Creighton ed., IRL Press, Oxford University Press, pp. 93-115). To prepare polyclonal antibodies, for example, the naturally derived protein of this invention prepared from the hippocampus tissue or the recombinant protein in combination with an adjuvant are used to immunize animals such as rabbit, guinea pig, goat, and such. By performing the immunization several times, the antibody titer can be elevated. After the final immunization, antiserum can be obtained by taking a blood sample from the immunized animal. This antiserum, for example, can be fractionated by ammonium sulfate precipitation or anion-exchange chromatography, and purified by affinity chromatography using protein A or immobilized antigens, to prepare polyclonal antibodies. It is also possible to use the partial peptide of the protein of this invention as the antigen. On the other hand, to prepare a monoclonal antibody, for example, the protein of this invention or its partial peptide is used to immunize the immunization animal in the same manner as described above, and after the final immunization, the spleen or the lymph nodes are obtained from the immunized animal. Antibody producing cells contained within the spleen or lymph nodes are fused with myeloma cells using polyethylene glycol, and such, to prepare hybridomas. The hybridomas of interest are screened, then cultivated, and from this culture supernatant, monoclonal antibodies can be prepared. Monoclonal antibodies can be purified, for example, through fractionation by ammonium sulfate precipitation and anion-exchange chromatography, and by affinity chromatography purification using protein A or immobilized antigens.

Antibodies thus prepared are used for the affinity purification of the proteins of this invention. They can also be used for the test and diagnosis of disorders caused by abnormal expression and structural abnormality of the proteins of this invention and for detection of the expression level of the protein, etc.

As indicated in the Examples, a decrease in the expression of the protein of this invention and deposits to the interstitium thereof are observed in Alzheimer's disease. Since the proteins of this invention are detected in the spinal fluid and sera, it is possible to test and diagnose diseases that cause accumulation of Aβ in the brain by detecting the proteins of this invention contained within these samples. The antibodies against the proteins of this invention are useful for this type of disease diagnostics.

The test for diseases that cause accumulation of Aβ in the brain, which uses the antibodies of this invention, can be carried out by a method comprising the steps of, (a) preparing samples from the subject, and (b) detecting the amount of protein of the present invention contained within the sample using antibodies against the protein. Diseases targeted by test of this invention are not limited as long as they are diseases that cause accumulation of Aβ in the brain, and may be, for example, senile dementia, Alzheimer's disease, Down's syndrome, hereditary cerebral hemorrhage, and cephalic contusion. As a sample to be prepared from the subject for testing, spinal fluid or serum is preferable.

The protein of this invention included in the sample can be detected, for example, by Western blotting, immunoprecipitation, ELISA, and such. The antibody used for detection may be either monoclonal antibody or polyclonal antibody. When the antibody is used as a testing reagent, pH buffer (for example, phosphate buffer, HEPES buffer, etc.) is used, and carriers (for example bovine serum albumin or gelatin, etc.), preservatives (sodium azide), and such may be mixed as necessary.

As a result of this detection, if an increase or decrease in the amount of antibody-reactive protein, abnormal molecular weight of the antibody-reactive protein, and/or abnormal molecular weight ratio of the respective proteins, are confirmed when comparing the sample of the subject to that of a healthy person, the subject is determined to have the above-mentioned disease, or is suspected of having the above-mentioned disease. Since this test is simple and places a small burden on the subject, it is an excellent method to test and diagnose diseases of the CNS.

Antibodies of this invention can be applied to the antibody treatment. For antibody treatment, they are preferably humanized or human antibodies. Such antibodies can be prepared by known methods (Parren, P. W. (1992) Hum. Antibodies Hybridomas 3, 137-145).

The present invention also relates to a method for screening a compound binding to the protein of this invention. The screening method of this invention comprises: (a) contacting a test sample with the protein of this invention or partial peptide thereof, (b) detecting the binding activity between the test sample and the protein of this invention or the partial peptide thereof, and (c) selecting a compound that has an activity to bind to the protein of this invention or the partial peptide thereof.

Test samples used for screening include, for example, cell extracts, expression products of a gene library, synthetic low molecular weight compounds, synthetic peptides, modified peptides, natural compounds, etc., but are not limited thereto. Those test samples used for screening may be labeled prior to use as the occasion demands. Labels include, for example, radioactive and fluorescent ones, etc., but are not limited to them.

Screening of proteins that bind to the protein of this invention can be carried out, for example, by applying the culture supernatant or cell extract of cells that are thought to express proteins that bind to the protein of this invention, to an affinity column that has an oligopeptide, and such, consisting of the 14 C-terminal amino acids (C14) of the protein of this invention, and by purifying the protein that specifically binds to this column. The screening of proteins that bind to the protein of this invention, or genes thereof, can be accomplished by utilizing, for example, West-western blot technique (Tarassishin, L. A. and Russell, W. C. (1997) Biochemistry (Mosc.) 62, 38-40; Matthews, D. A. and Russell, W. C. (1998) J. Gen. Viol. 79, 1671-1675) and two-hybrid system (Vidal, M. (1997) The Reverse Two-Hybrid System in "The Yeast Two-Hybrid System" (Bartel, P. and Fields, S. eds.) Oxford University Press, New York; Fields, S. and Song, O. K. (1995) Microbiology Rev. 59, 94; Vidal, M. et al. (1996) Proc. Natl. Acad. Sci. USA 93, 10321). Methods to isolate compounds that bind to the protein of this invention by high-throughput screening (Cerretani, M. et al. (1999) Anal. Biochem. 266, 192-197; Kenny, B. A. et al. (1998) Prog. Drug. Res. 51, 245-269; Gonzalez, J. E. and Negulescu, P. A. (1998) Curr. Opin. Biotechnol. 9, 624-631) using combinatorial chemistry techniques (Myers, P. L. (1997) Curr. Opin. Biotechnol. 8, 701-707; Campbell, D. B. (1997) Q. J. Nucl. Med. 41, 163-169), and such, are also well known to those skilled in the art.

In addition, the present invention relates to a method to screen compounds that promote or inhibit peptidase activity of the protein of this invention. This method uses as an index, the substrate cleaving activity of the protein of this invention, and specifically comprises the steps of, (a) contacting the protein of this invention with its substrate in the presence of a test sample, (b) detecting the cleavage of the substrate, and (c) selecting a compound comprising the activity to increase or decrease substrate cleavage caused by the protein of this invention, in comparison to the cleavage in the absence of the test sample (control).

Test samples used for this screening method include, for example, cell extracts, expression products of a gene library, synthetic low molecular weight compounds, proteins, natural or synthetic peptides, natural products, sera, etc., but are not limited to them. The test samples can be compounds isolated by the above-described screening method monitoring the binding activity of the compounds to the protein of this invention. The protein of this invention to be used for screening may be a natural protein or a recombinant protein.

Brain APP is preferred as a substrate. Natural brain APP can be prepared by the method described in the Examples. In addition, as long as the protein of this invention can show a cleaving activity, partial peptides of brain APP, other APP isoforms and APP-like polypeptides, and oligopeptides synthesized to contain the cleavage site of the substrate may be used.

Cleavage of the substrate can be detected, for example, by incubating the protein of this invention with a substrate, then performing SDS-PAGE, and finally performing Western blotting using an antibody against the substrate. Alternatively, when using a synthetic oligopeptide as a substrate, detection can be carried out by Tris-tricine-type PAGE, or by thin-layer chromatography (TLC), and such, by labeling the N terminus, the C terminus, and such in advance. Otherwise, if one end of the substrate peptide is immobilized onto a support such as a microplate, and the other end is labeled, substrate fragments could be easily detected If cleavage of the substrate by the protein of this invention is promoted when a test sample is present, compared to when the test sample is absent, that compound is determined to be the compound promoting substrate-cleaving activity of the protein of this invention. Conversely, if substrate cleavage by the protein of this invention is inhibited, when the test sample is present, that compound is determined to be the compound inhibiting substrate-cleaving activity of the protein of this invention. In the present invention, "inhibiting substrate-cleaving activity" includes cases where the cleaving activity is completely inhibited and cases where the inhibition is partial.

To determine the substrate cleavage site by the protein of this invention, for example, the cleavage site is estimated by first incubating brain APP and the protein of this invention, then upon separating the cleaved brain APP by SDS-PAGE, Western blotting is carried out using domain-specific antibodies for APP (for example, for Aβ, Aβ 1-17 antibody, Aβ 17-24 antibody, Aβ 1-40 C-terminal antibody, Aβ 1-42 C terminal antibody, etc.). Next, as an advanced system, the substrate fragments cleaved by the protein of this invention are purified, and by performing N-terminal or C-terminal amino acid sequencing, the cleavage site can be determined. Alternatively, the cleavage site can be estimated using a synthetic oligopeptide (for example, Aβ 1-42, etc.) as a substrate, and upon incubation with the protein of this invention, free amino acids that are digested from the C terminus can be measured qualitatively and quantitatively by an amino acid analyzer.

The protein of this invention and the compounds isolated by the screening method of this invention may be applied, for example, as agents for regulating Aβ production, and as drugs for preventing and treating cerebral diseases in which the protein of the present invention is involved (for example, diseases causing Aβ accumulation, such as Alzheimer's disease).

When the proteins of this invention or compounds isolated by the screening methods of this invention are used as drugs, they may be administered to patients as they are or as pharmaceutical preparations produced by known methods. They can be formulated together with, for example, pharmaceutically acceptable carriers or media such as sterilized water, physiological saline, vegetable oil, emulsifiers, suspending agents, surfactants, stabilizers, etc. They may be administered to patients by methods well known in the art, for example, by intra-arterial, intravenous, subcutaneous injection. They can also be administered intranasally, intrabronchially, intramuscularly, or orally. Doses may vary depending on the body weight and age of patients as well as administration method, and such, and can be suitably selected by those skilled in the art. When the compound is encoded by DNA, gene therapy may be performed by inserting the DNA into a vector for gene therapy. Doses and method for its administration may vary depending on the body weight, age, symptoms, and so on of patients, but can be suitably selected by those skilled in-the art.

In addition, the present invention relates to a kit for screening a compound that promotes or inhibits peptidase activity of the protein of this invention, wherein said kit comprises the protein. Examples of the protein of this invention in the kit of this invention may be a purified or crudely purified protein, may be in a form expressed outside or inside a desired cell (including a transformant made to express the protein), or in a form bound to a support. The kit of this invention preferably comprises a substrate as another element in addition to the protein preparation mentioned above. As substrate., brain APP is preferred, although there is no limitation as long as the protein of this invention shows cleaving activity. Natural brain APP can be prepared by the method described in the Examples. In addition, partial peptides of brain APP, other APP isoforms and APP-like polypeptides, and oligopeptides synthesized to contain a cleavage site of a substrate may be included as substrates. The substrate may be labeled. Furthermore, buffer for the reaction between the protein of this invention and the substrate, washing solution, and a reagent for detecting cleavage of the substrate may be included.

BRIEF DESCRIPTION OF THE DRAWINGS

FIG. 3 shows nucleotide and deduced amino acid sequences of prepro-HBCPB-cDNA (SEQ ID NO:1). Numbers on the left indicate the cDNA nucleotide residues, those on the right the deduced amino acid residues. Arrowheads show the cleavage sites at which the hydrophobic signal (22 amino acid residues) and activation (92 amino acid residues) peptides are predicted to be released from the preproenzyme. The amino acid sequence identified in the 30 kDa protein (mature enzyme) is underlined. The stop codon and polyadenylation signal are double underlined. N-linked glycosylation sites are indicated by a closed circle under the asparagine residue. The amino acid residue implicated in zinc-binding (circles around amino acid residues) and substrate-binding (squares around amino acid residues) for tissue CPB and HPCPB are indicated. These sequence data have been submitted to the DDBJ/EMBL/GenBank databases under accession number AB011969.

FIG. 4 shows molecular characterization of prepro-HBCPB. (A), comparative schematic presentation of the structures of prepro-HBCPB and prepro-HPCPB. (B), alignment of the C-terminal 14 amino acid residues unique to HBCPB with homologous computer-searched peptides(SEQ ID NOs: 9-12). Identical amino acids are surrounded by a box. (C), RT-PCR analysis of human hippocampal RNA for HBCPB. Migration positions of the DNA molecular mass markers are given in bp. Arrowheads indicate migration positions of the 1077 bp band of the synthesized HBCPB-cDNA (left) and the 538 bp band corresponding to the 3'-terminal portion of HBCPB-cDNA (right).

FIG. 6 shows preparation of a polyclonal antibody against prepro-HBCPB and Western blot analysis. (A), SDS-PAGE profile of the fraction bound to benzamidine-Sepharose. Left, migration positions of the molecular mass markers as in FIG. 1A. Arrowhead, migration position of the 40 kDa protease. (B), Western blot analysis using the antibody of fractions separated by native-PAGE. Fractions 17 through 21 (lanes 1 through 5) were separated by SDS-PAGE. Left numerals and arrowhead are as in A. (C), Western blot analysis of hippocampal homogenate using the anti prepro-HBCPB antibody (lanes 1 through 4) or anti C14 antibody (lanes 5 through 7). Left numerals are similar to A. Arrowheads indicate the migration positions of the 40 kDa protease (large arrowhead) and 30 kDa mature form (small arrowhead).

FIG. 10 is a photograph indicating an immunohistochemical analysis of a rat testis. The cytoplasm of the Leydig's cells of the interstitium is darkly stained by anti-C14 module antibody (recognizing the C-terminal portion of human brain CPB). The magnification of the top and bottom photographs is 200-fold and 400-fold, respectively.

BEST MODE FOR CARRYING OUT THE INVENTION

The present invention will be explained in detail below with reference to examples, but it is not to be construed as being limited thereto.

EXAMPLE 1

Figure 1:
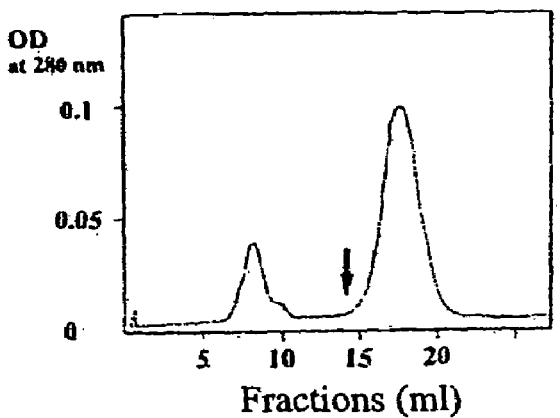
FIG. 1 shows APP-degrading activity from human hippocampal homogenate. (A), Native-PAGE profile of the fraction bound to a benzamidine-Sepharose 6B affinity column. Coomassie brilliant blue staining. Left, migration positions of the molecular mass markers in kilo Daltons: 220 kDa, myosin; 97 kDa, phosphorylase b; 67 kDa, bovine serum albumin; 46 kDa, ovalbumin; 30 kDa, carbonic anhydrase; 21 kDa, trypsin inhibitor. (B), SDS-PAGE analysis of the proteins fractionated by preparative native-PAGE. Only one in three fractions was loaded on a parallel well, separated and made visible by silver staining. (C), Mono S ion-exchange chromatography of fraction 19 separated by native-PAGE. Ordinate, optical density (OD) at 280 nm. Abscissa, fractions in ml. Arrow indicates the fraction position at which the elution buffer was added.

Preparation of 40 kDa Protease from Hippocampal Homogenate and Analysis of APP-proteolysis Ten brain samples were obtained at autopsy within 5 h of death from five patients who died of non-neurological disorders (55-82 y) and five who died of sporadic AD (60-84 y). Temporal lobe slices were taken, frozen in liquid nitrogen and stored at −110° C. To prepare the homogenate, the hippocampal region (approximately 4 g) of the frozen sample was excised, then thawed in 15 ml of sterile homogenization buffer consisting of 50 mM Tris-HCl (pH 7.5)/1 mM EDTA/2 mM phenylmethanesulfonyl fluoride, after which it was homogenized on ice in a Dounce homogenizer. The homogenate was centrifuged at 39,000 g for 30 min. The supernatant was precipitated with 40% ammonium sulfate, and the precipitate dialyzed against ice-cold homogenization buffer. The dialysate was used as the hippocampal homogenate. The natural brain APP was prepared by immunoprecipitation of the homogenate using anti cAPP antibody (Matsumoto, A. and Fujiwara, Y. (1991) Biochem. Biophys. Res. Commun. 175, 361-365) as described (Matsumoto, A. and Fujiwara,Y., 1993, Eur. J. Biochem. 217: 21-27). The hippocampal homogenate (approximately 10 mg per preparation) was chromatographed in a benzamidine-Sepharose™ 6B affinity column (Amersham Pharmacia, UK), which captures a wide range of serine proteases, using the equilibration buffer 20 mM Tris-HCl (pH 7.5). After collecting the pass-through fraction, the column was vigorously washed with the equilibration buffer until the optical density of the eluant at 280 nm reached the base-line level. The fraction bound to the column was recovered using an elution buffer consisting of 20 mM Tris-HCl (pH 7.5) and 0.2 M NaCl, then it was dialyzed against ice-cold 10 mM Tris-HCl (pH 7.5), and lyophilized. The native-PAGE profile of the total bound fraction by Coomassie brilliant blue staining is shown in FIG. 1A.

A native polyacrylamide gel electrophoresis (native-PAGE) was conducted without SDS to separate the bound fraction without losing proteolytic activities. A preparative polyacrylamide gel electrophoresis apparatus with a liquid-phase collecting device (Biophoresis™ 3, Atto, Japan) and a Tris-glycine buffer system were used for native-PAGE (Smith, J. A. (1989) Electrophoretic separation of proteins. In Ausubel, F. M. et al. (eds.), Current Protocols in Molecular Biology., John Wiley and Sons, New York, USA, pp. 10.2.1-10.2.9). Approximately 3 mg of the bound fraction was separated by the native-PAGE into 61 fractions ranging in molecular mass from 20 to 100 kDa. A portion of each fraction then was checked for its protein component by SDS-PAGE and the component made visible by silver staining (FIG. 1B).

In the proteolytic analysis of the fractions for natural brain APP, approximately 0.1 pmol of natural brain APP prepared from human hippocampus was incubated at 37° C. for 3 h with each fraction (approximately 0.05 pmol) in the presence of 1 mM Zn²⁺. To obtain proteolytic activities of interest, each reaction mixture was loaded in parallel wells for SDS-PAGE then subjected to Western blot analysis using anti Aβ 1/14 antibody (Calbiochem) as follows.

After separation of proteins by SDS-PAGE, proteins on the gel was blotted onto a Hybond C nitrocellulose membrane (Amersham Pharmacia, UK), after which non-specific binding was blocked by immersing the membrane in 5% bovine serum albumin for 1 h in Tris-buffered saline: 100 mM Tris-HCl (pH 7.5), 140 mM NaCl and 0.1% Tween 20. The membrane next was washed for 45 min with three changes of the above buffer then incubated at 4° C. for 16 h with the first antibody (anti Aβ 1/14 antibody) appropriately diluted with Tris-buffered saline. After again washing it as above, the membrane was incubated at room temperature for 1 h with a horseradish peroxidase-labeled anti rabbit second antibody diluted 1:2000. After the washing, signals were detected on X-ray film using an ECL chemiluminescence detection system (Amersham Pharmacia, UK).

Of the 61 fractions analyzed, fraction 19 with a molecular mass of about 40 kDa and fraction 11 with a molecular mass of about 30 kDa had similar proteolytic activities. In the analysis, fraction 19 did not have homogeneity in its protein component, and fraction 11, although homogeneous in its components, lost its activity within 30 min at room temperature or during long-term storage (2 w) at −20° C. Fraction 19 with the 40 kDa molecular mass with proteolytic activity therefore was further purified.

A sufficient amount of fraction 19 was collected by preparative electrophoresis (totally five rounds) (FIG. 1B). To homogenize fraction 19 (approximately 8 μg), it was run through a 1 ml Mono S ion-exchange column with 20 mM Tris-HCl (pH 7.5) as the equilibration buffer. After washing, the bound fraction was recovered with 20 mM Tris-HCl (pH 7.5)/0.2 M NaCl as the elution buffer. The 40 kDa proteolytic activity from fraction 19 was trapped in the column and recovered by elution, whereas the co-migrating protein passed through (FIG. 1C). It then was dialyzed and lyophilized as above and used as HBCPB standard. Recovery of the HBCPB from the fraction bound to the benzamidine-Sepharose column (approximately 15 mg) was 2 μg (approximately 5 pmol).

Figure 2:
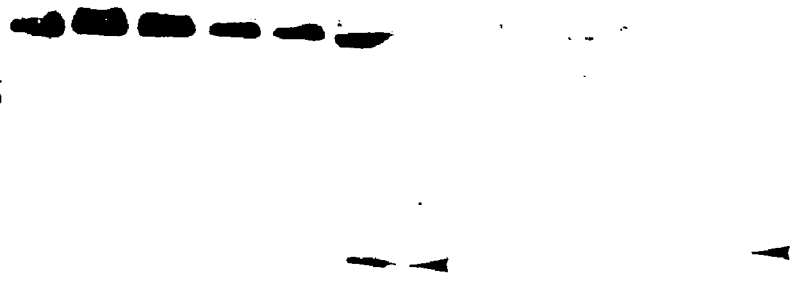
FIG. 2 shows brain APP degrading activity of the purified 40 kDa protein. Approximately 0.1 pmol of natural APP (except lane 3) or APP pretreated with chondroitinase ABC (CDR-ABC) (lane 3) was treated with the 40 kDa protease (approximately 0.05 pmol, lanes 2, 3, 4, 6, 7, 8, 9, and 10; approximately 0.01 pmol, lane 5), in the presence or absence of 1 mM EDTA (lane 2) or 1 mM potato carboxypeptidase inhibitor (CPI) (lane 4). Analyses were also conducted under the coexistence of anti 40 kDa protease antibody (lane 9) or anti C14 antibody (lane 10) (1/50 volume). After Tris-tricine SDS-PAGE, the blot corresponding to lanes 1 through 6 was analyzed using anti Aβ 1/14 antibody, and one corresponding to lanes 7 and 10 using anti APP-CT antibody. Left, migration positions of the molecular mass markers in kilo Daltons: 46 kDa, ovalbumin; 21 kDa, trypsin inhibitor; 14 kDa, α-lactoalbumin; 6.5 kDa, myoglobin II; 3.4 kDa, myoglobin I. Arrowhead indicates the migration position of the 5.5 kDa Aβ peptide.

The brain APP substrate (approximately 0.1 pmol) was treated with the 40 kDa protease (0.005 to 0.1 pmol) at 37° C. for 3 h in the presence of 1 mM $Zn^{2+}$ to analyze the isolated 40 kDa protease. The reaction product analyzed by Western blotting with anti Aβ 1/14 antibody (FIG. 2). Under these reaction conditions, the 40 kDa protein degraded natural brain APP, generating a 5.5 kDa fragment as the major component of the 3 to 11 kDa Aβ-containing peptides (FIG. 2, lanes 5 and 6). The reaction was completely inhibited by 5 mM EDTA (FIG. 2, lane 2) and by 1 mM potato carboxypeptidase inhibitor (BioPur, Switzerland) (FIG. 2, lane 4). Pretreatment of the APP with chondroitinase ABC was done by incubating 0.1 pmol natural brain APP with 0.5 pmol protease-free chondroitinase ABC (Seikagaku, Japan) at 37° C. for 3 h in 20 mM Tris-HCl (pH 7.0) in the absence of $Zn^{2+}$ which inhibits the enzyme activity. The reaction mixture was incubated at 65° C. for 15 min to denature the enzyme. A proteolysis reaction was then conducted as described above, and as a result, it was shown that the reaction is almost completely inhibited (FIG. 2, lane 3). When anti APP-CT antibody which is raised against the oligopeptide $NH_2$-TPEERHLSKMQQNGY-ENPTYKFFE-COOH (SEQ ID NO: 5) ($668^{th}$ to $691^{st}$ amino acid residues of APP695), which corresponds to a part of the cytoplasmic domains of APP, was used for Western blot analysis, the 5.5 kDa fragment was a major cleavage product (FIG. 2, lane 8). This proteolysis was completely inhibited in the presence of anti 40 kDa protease antibody or anti C14 antibody (1/50 volume of the reaction mixture) (FIG. 2, lanes 9 and 10).

Detection by both the anti Aβ 1/14 and anti APP-CT antibodies of the 5.5 kDa fragment as a major cleavage product from brain APP (FIG. 2) suggests that this fragment is generated by cleavage in the vicinity of the Aβ N-terminus and in the APP cytoplasmic domain in the vicinity of the transmembrane portion, spanning almost intact Aβ. HBCPB does not appear to have the α-secretase-like activity that cleaves the 15 to 17 amino acid residues of Aβ, therefore there is no C-terminal APP fragment carrying the anti APP-CT domain.

EXAMPLE 2

Molecular Cloning and Structural Analysis of the cDNA Encoding the 40 kDa Protease Each 40 and 30 kDa protein was immobilized on an Immobilon $p^{SQ}$ filter (Millipore, USA) then subjected to Edman degradation to isolate a cDNA clone by screening the hippocampal cDNA library with an oligonucleotide synthesized through N-terminal amino acid sequencing. Micro-sequencing analysis of the 40 kDa protein was unsuccessful, possibly owing to a blocked N-terminus. Results of sequencing of the 30 kDa protein are shown in Table 1. In this table, yields of respective amino acids in each cycle are shown by pmol. Most abundantly recovered amino acids are underlined. Each amino acid is abbreviated as follows: D: aspartic acid, E: glutamic acid, N: asparagine, S: serine, T: threonine, Q: glutamine, G: glycine, H: histidine, A: alanine, Y: tyrosine, R: arginine, P: proline, M: methionine, V: valine, W: tryptophan, K: lysine, F: phenylalanine, I: isoleucine, L: leucine.

TABLE 1

Yields of Edman degradation product prepared from the 30 kDa protein (pmol)

|   | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| D | 2.7 | 3.2 | 3.1 | 2.7 | 4.9 | 3.3 | 3.2 | 3.4 | 3.4 | 4.0 | 2.2 | 2.4 | 3.3 | 2.1 | 2.1 |
| E | 5.4 | 4.5 | 4.9 | 3.4 | 3.9 | 4.3 | <u>33.0</u> | 6.0 | 4.7 | 3.4 | 4.2 | 4.6 | 3.7 | <u>22.1</u> | 5.4 |
| N | 5.1 | 4.4 | 4.0 | 2.6 | 1.8 | 3.5 | 2.9 | 2.9 | 2.5 | 3.4 | 2.5 | 2.4 | <u>3.3</u> | 2.5 | 4.5 |
| S | 5.1 | <u>24.6</u> | 7.3 | <u>20.6</u> | 6.3 | 3.1 | 3.2 | 3.8 | 2.9 | 2.8 | <u>23.3</u> | 5.4 | 2.9 | 3.7 | 4.1 |
| T | 3.8 | 3.4 | 3.6 | 2.3 | 2.5 | 2.4 | 2.5 | 2.6 | 2.4 | 3.3 | 3.5 | 2.4 | 2.5 | 2.3 | 2.3 |
| Q | 5.5 | 4.5 | 3.8 | 2.9 | 2.9 | 3.7 | 4.8 | <u>25.4</u> | 3.6 | 3.4 | 2.4 | 3.7 | 3.6 | 3.8 | 3.4 |
| G | 4.3 | 4.4 | 3.4 | 3.2 | 3.0 | 2.4 | 2.5 | 3.3 | 4.8 | 2.6 | 4.1 | 3.3 | 3.5 | 3.4 | 2.5 |
| H | 3.6 | 2.4 | 1.7 | 1.9 | 2.5 | 2.4 | 1.9 | 3.8 | 3.4 | <u>22.0</u> | 5.4 | 3.5 | 3.7 | 3.9 | 2.7 |
| A | <u>34.1</u> | 6.5 | <u>29.9</u> | 4.1 | 5.2 | 4.7 | 3.6 | 3.9 | 4.9 | 3.9 | 7.4 | 4.9 | 6.6 | 3.9 | 4.9 |
| Y | 7.5 | 5.3 | 5.0 | 5.2 | <u>41.1</u> | <u>29.5</u> | 6.4 | 4.0 | <u>23.7</u> | 5.7 | 3.9 | 3.4 | 2.3 | 2.5 | 2.6 |
| R | 3.4 | 3.8 | 2.4 | 3.1 | 2.9 | 3.5 | 2.3 | 3.4 | 3.2 | 3.0 | 3.5 | 3.2 | 3.3 | 3.4 | 3.4 |

TABLE 1-continued

Yields of Edman degradation product prepared from the 30 kDa protein (pmol)

|   | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| P | 3.9 | 3.2 | 3.2 | 3.5 | 2.4 | 2.8 | 3.1 | 3.3 | 3.6 | 3.9 | 2.4 | 2.9 | 2.3 | 2.6 | 2.5 |
| M | 2.4 | 2.0 | 1.3 | 1.0 | 1.4 | 1.6 | 1.4 | 1.4 | 1.1 | 2.3 | 2.0 | 2.6 | 1.9 | 2.3 | 2.1 |
| V | 3.2 | 3.0 | 3.1 | 3.7 | 3.0 | 3.5 | 3.6 | 3.8 | 4.1 | 4.3 | 2.4 | 3.9 | 4.0 | 3.1 | 3.6 |
| W | 0 | 0 | 0 | 0 | 0 | 0 | 0 | 0 | 0 | 0 | 0 | 0 | 0 | 0 | 0 |
| K | 3.6 | 2.4 | 3.9 | 3.8 | 3.8 | 3.3 | 3.0 | 3.5 | 2.9 | 2.5 | 2.0 | 2.1 | 1.9 | 2.5 | 2.9 |
| F | 2.9 | 1.4 | 1.4 | 1.5 | 1.8 | 1.9 | 1.9 | 1.5 | 2.0 | 1.5 | 2.3 | 3.0 | 2.2 | 2.7 | 3.1 |
| I | 3.5 | 3.3 | 3.6 | 4.2 | 3.5 | 2.9 | 3.4 | 3.4 | 3.1 | 3.1 | 4.5 | 3.4 | 4.4 | 4.8 | <u>24.1</u> |
| L | 2.5 | 2.4 | 2.5 | 3.7 | 3.5 | 4.1 | 3.6 | 2.4 | 2.2 | 2.3 | 2.6 | <u>22.3</u> | 4.4 | 3.6 | 2.7 |

As a result, it was showed that the 30 kDa protein is identical to the N-terminal sequence of the mature form of human plasma CPB. To resolve the ambiguity about the identity of the 30 kDa protein and clarify the relationship between the 40 and 30 kDa proteins, molecular cloning for the cDNA encoding the 40 kDa protein was done by two methods; RT-PCR analysis of hippocampal mRNA using amino acid sequencing results, and immunological screening of the human hippocampal cDNA library.

Poly(A)+ RNA (poly(A)-rich RNA) was prepared from the frozen hippocampus blocks of the two brains using a quick-Prep™ mRNA Purification Kit (Amersham Pharmacia, UK). The human hippocampal cDNA library was constructed by the method of Gubler and Hoffmann (Gubler, U. and Hoffman, B. J. (1983) Gene, 25, 263-269). First strand cDNA was synthesized from 1.5 μg poly(A)+ RNA using cloned Moloney murine leukemia virus reverse transcriptase (FPLC-pure™, Amersham Pharmacia, UK) which is primed with synthetic oligo(dT). Second strand cDNA then was synthesized from the first-strand DNA using cloned Escherichia coli DNA polymerase I (Takara, Japan) in the presence of cloned Escherichia coli ribonuclease H (Amersham Pharmacia, UK). The double-strand cDNA was blunt-ended by T4 phage polymerase (Takara, Japan), and its EcoRI site modified using Escherichia coli EcoRI methylase (Takara, Japan) then ligated with an EcoRI linker. The cDNA was ligated using a DNA ligation kit (Takara, Japan) with the λgt11 phage vector EcoRI arm then packaged in vitro (PhageMaker™, Takara, Japan). The estimated efficiency of this library construction was 9.0×10⁵ plaque forming units (pfu)/μg poly(A)+ RNA with Escherichia coli Y1090r⁻ as the host bacteria.

Immunological screening of the λgt11-based human hippocampal library was done with the anti 40 kDa protein polyclonal antibody (diluted 1:1500) (described below) (St John, T. P. (1989) Screening with antibodies. In Ausubel, F. M. et al. (eds.), Current Protocols in Molecular Biology., John Wiley and Sons, New York, USA, pp. 6.7.1-6.7-5). Three positive clones were isolated from phage, screened 3×10⁵ plaque forming units (pfu). Because the restriction endonuclease digestion profiles of the DNAs were very similar, the structure of the clone with the longest insert was analyzed. Nucleotide sequencing was done in a PRISM™ automatic sequencer (Applied Biosystems, USA).

1544 bp cDNA (SEQ ID NO: 1) isolated above, carries a single open reading frame 1083 bp long which predicts the encoding of 360 amino acid residues (SEQ ID NO: 2) (FIG. 3). Computer-assisted homology analysis showed that the cDNA has a homology close to that of human plasma CPB (HPCPB) (Eaton, D. L. et al. (1991) J. Biol. Chem., 266, 21833-21838). Other homologous proteins identified are tissue-type CPB (Yamamoto, K. K. et al. (1992) J. Biol. Chem., 267, 2575-2581) and mast cell CPB (Goldstein, S. M. et al. (1989) J. Clin. Invest., 83, 1630-1636). A comparison of the structures of prepro-HPCPB and the human brain protease (prepro-HBCBP) showed that the latter (prepro-HBCPB) also has the common CP structure; the presence of a signal (22 amino acids) and an activation (92 amino acids) peptide in front of the mature enzyme (246 amino acids for HBCPB and 317 amino acids for HPCPB) (FIG. 4A). The difference is in the sequence of the mature enzyme: Firstly, the 37 amino acid residues in the middle of the mature plasma enzyme, that correspond to the 198 to 334th amino acid residues of prepro-HPCPB (the 633 to 743rd nucleotide residues of prepro-HPCPB-cDNA), are absent from HBCPB. Secondly, the absence of nucleotides corresponding to those of the 1190th to 1241st residues of prepro-HPCPB-cDNA induced the deletion of 40 amino acid residues, (the 384th to 423rd amino acids of prepro-HPCPB), and a frame-shift which generates a unique 14 amino acid residue in the C-terminus of prepro-HBCPB. The former alternation eventually induces an in-frame deletion, and the latter another deletion followed by an amino acid change due to translation of a different frame, including that of the 3' non-coding region (4 amino acids) of prepro-HPCPB-mRNA and a different stop codon.

Peptide sequences homologous to the C-terminal 14 amino acid residue (C14) unique to HBCPB were searched for in the current database of peptides and proteins (FIG. 4B). The most homologous peptide is in the domain of the chloroplast ATP synthase γ subunit of various plant species (Inohara, N. et al. (1991) J. Biol. Chem., 266, 7333-7338) The homology of the C14 peptide with these plant peptides that are located in the N-terminal area of the light-dependent regulation domain of chloroplasts is very high (over 85%). In addition to having 9 identical amino acids, the fourth amino acid (proline), and the fifth (valine) and thirteenth (leucine) are replaced respectively by the functionally-identical (neutral as well as hydrophobic) amino acids valine, threonine and proline.

Independent to immunological screening, the RT-PCR method and 3' RACE (rapid amplification of cDNA ends) system (GIBCO-BRL, USA) were used to obtain cDNA encoding the brain CPB. The template RNA, which differed from that used in the library construction, was hippocampal poly(A)+ RNA prepared from three normal brains, cDNA was synthesized by SUPERSCRIPT™ reverse transcriptase (GIBCO-BRL, USA) using the sense oligonucleotide (5'-GCCTCCGCATCGTACTATGAACAGTATCAC-3'/SEQ ID NO: 6) synthesized through the amino acid sequencing result (Table 1) and the adapter primer with oligo(dT) stretch as the antisense primer. As a result, only a single 1077 bp band was detected as a RT-PCR product (FIG. 4C, lane 1). After purification by HPLC the PCR product was subjected to sequence analysis. Nucleotide sequencing was done in a PRISM™ automatic sequencer (Applied Biosystems, USA).

The sequence was identical to nucleotide 360 to 1436 of prepro-HBCPB-cDNA, corresponding to the mature form of HBCPB. That is, cDNA obtained by either of the two types of cloning procedures, were shown to be derived from the same mRNA in the hippocampus. In addition, from this result, it can be supposed that the 30-kDa protein is encoded by the same gene as the 40-kDa protein, and that the 30-kDa human brain CPB mature protein is produced by cleavage of the N-terminal portion of the 40-kDa protein.

EXAMPLE 3

Northern Blot Analysis in Various Tissues

RNA samples from various organs were analyzed for the expression of prepro-HBCPB-mRNA or its homologue. Poly (A)+ RNAs from human brain (hippocampus), heart, pancreas, kidney, liver and spleen were prepared from normal autopsy samples by loading 1 μg poly (A)+ RNA on a 1% agarose gel cast in MOPS (3-[N-morpholino]propane-sulfonic acid) buffer: 20 mM MOPS (pH 7.0), 5 mM NaOAc and 1 mM EDTA containing 6.6% formaldehyde. After electrophoresis, the gel was transferred onto a nylon membrane (Hybond N+, Amersham Pharmacia, UK) by capillary blotting and immobilized by baking. The blot was then hybridized at 68° C. for 1 h in ExpressHyb™ hybridization solution (Clontech, USA)

The probe was the 538 bp C-terminal portion of prepro-HBCPB cDNA, synthesized by the PCR with 5'-GGTTCAT-AGGCCATAATCGAATGT-3' (SEQ ID NO: 7) as the sense-primer (corresponding to nucleotides 596 to 618 of the cDNA) and 5'-TCAGGGGCATTAAACATTCCTAAT-3' (SEQ ID NO: 8) as the antisense-primer (corresponding to nucleotides 1135 to 1112 of the cDNA), and TakaraTaq™ recombinant Taq polymerase (Takara, Japan) (FIG. 4C, lane 2). The human β-actin cDNA probe (Clontech, USA) was used as the control. These probes were radio-labeled with [α-$^{32}$P]dCTP using a Random Primer DNA Labeling Kit (Takara, Japan). The blot was washed twice at room temperature in 2×SSC for 20 min, then in 2×SSC, 0.1% SDS and twice at 65° C. for 40 min in 0.1×SSC, 0.1% SDS.

Figure 5:
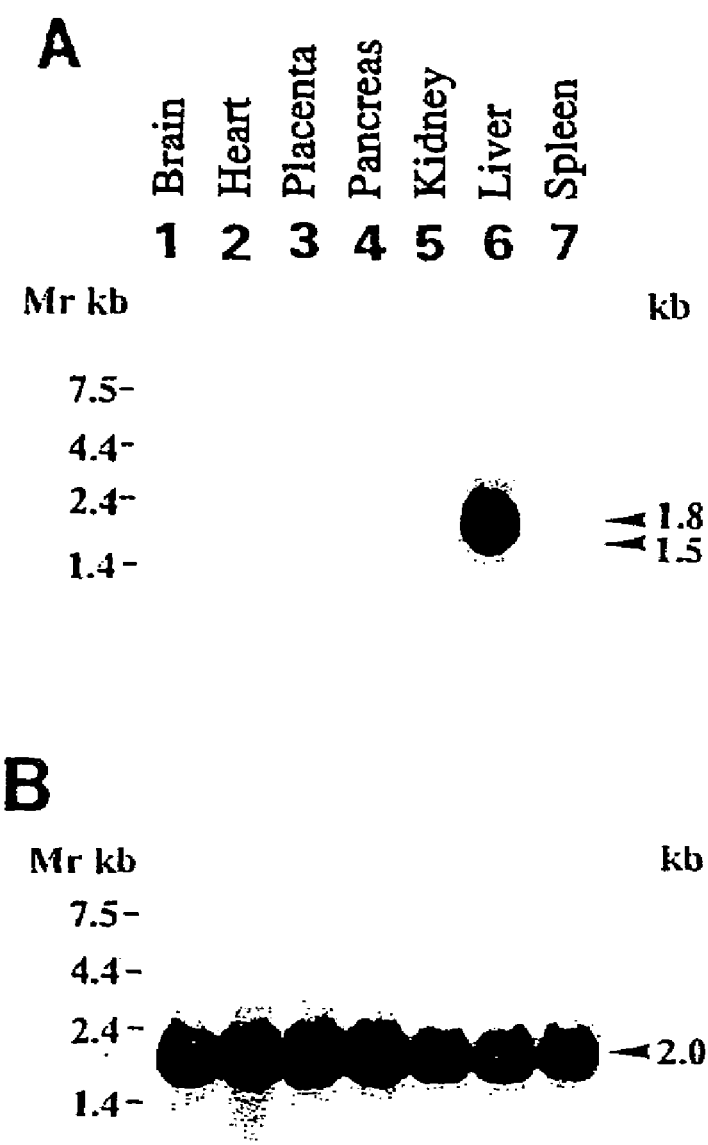
FIG. 5 shows Northern blot analysis of human mRNA from various organs. Poly(A)+ RNAs prepared from 20 μg of the total RNA from human brain (hippocampus) (lane 1), heart (lane 2), placenta (lane 3), pancreas(lane 4), kidney (lane 5), liver (lane 6) and spleen (lane 7) were loaded in parallel wells of a denaturing agarose gel in duplicate (A and B). (A), autoradiogram probed with the $^{32}$P-labeled 538 bp fragment of prepro-HBCPB-cDNA. (B), autoradiogram probed with the ³²P-labeled β-actin cDNA probe. Left, migration positions of the RNA molecular mass markers in kb. Arrowheads, migration positions of the 1.8 kb prepro-HPCPB mRNA and 1.5 kb prepro-HBCPB mRNA (in A) and 2.0 kb human β-actin mRNA (in B).

As expected from the high homology of the DNA sequence of prepro-HBCPB-cDNA to that of prepro-HPCPB-cDNA (FIG. 4A), human liver showed abundant expression of the 1.8 kb band with this probe (FIG. 5, lane 6). In contrast, human brain RNA expresses a 1.5 kb band with much less intensity (FIG. 5, lane 1). RNA samples derived from the heart, placenta, pancreas, kidney and spleen did not express the signal with this probe (FIG. 5, lanes 2, 3, 4, 5 and 7). The difference in the sizes of mRNA signals in the brain and liver agrees well with that of the coding size of the cDNAs of prepro-HBCPB and prepro-HPCPB, indicative that this probe segregates tissue-type CPs that are abundantly expressed in the pancreas.

EXAMPLE 4

Preparation of Polyclonal Antibodies Against the 40 kDa Protease and C-terminal 14 Amino Acid Peptide of the Protease, and Western Blot Analysis The fraction bound to the benzamidine-Sepharose column was separated by preparative SDS-PAGE and collected in a liquid-phase collecting device to prepare the 40 kDa protease in quantity sufficient (2 mg) to immunize two New Zealand White rabbits. The SDS-PAGE profile indicates that the 40 kDa protein was separated to homogeneity (FIG. 6A). Unlike native-PAGE, no further separation using ion-exchange chromatography was required to bring the denatured 40 kDa protein to homogeneity. Using the 40 kDa protease as an antigen, anti prepro-HBCPB polyclonal antibody was raised against rabbit. Antiserum was obtained from rabbit, and the IgG fraction was purified by using EZ Prep (Pharmacia). A titer check of its specificity to the antigen indicated a 2000-fold sensitivity over preimmune sera (control antibody). Anti-C14 antibody was raised against the oligopeptide NH$_2$-SNP-PVEKLLPLSLK-COOH (SEQ ID NO: 9) corresponding to the unique C-terminal 14 amino acid residues of the protease. The oligopeptide was conjugated to keyhole limpet hemocyanin (Calbiochem, USA) using 3-maleimidobenzoic acid N-hydroxysuccimide ester (Sigma, USA) and used to immunize rabbits. The antiserum obtained was affinity-purified in an oligopeptide-conjugated Sepharose CL-4B column. A titer check of its specificity indicated 1500-fold sensitivity to the oligopeptide antigen over that of preimmune sera (control antibody).

The specificity of the antibody was checked by Western blot analysis similar to Example 1 with the fractions separated by native-PAGE and SDS-PAGE as the antigens (FIG. 6B). This anti prepro-HBCPB polyclonal antibody detects a single 40 kDa band, the highest intensity being in fraction 19, in which the original proteolytic activity is found (FIG. 1B). In the analysis of the hippocampal homogenate from various brain samples, this antibody detected 40 and 30 kDa bands (FIG. 6C, lanes 1 through 4). This result is relevant to the finding that the two native-PAGE fractions corresponding to the 40 and 30 kDa molecular masses have APP-degrading activity and that the 30 kDa protein is the mature form of prepro-HBCPB. Western blot analysis using the anti C14 antibody gave essentially the same results for brain samples (FIG. 6C, lanes 5 through 7) but no immunoreactive bands were detected in the liver human homogenate. This implies that the anti C14 antibody recognizes HBCPB in the human brain.

When the spinal fluid and peripheral blood serum from a normal person and from an AD patient were used as samples for analysis by Western blot technique using the anti-C14 antibody, immunoreactivity of the anti-C14 antibody was detected in all samples. In addition, in the peripheral blood serum, immunoreactivity tended to increase with age.

EXAMPLE 5

Immunohistochemical Analysis

Using the antibody that specifically recognizes human brain CPB (HBCPB) produced in Example 4, immunohistochemical analysis described below was performed. Immediately after autopsy, the samples used for the immunohistochemical study were fixed in 10% formaldehyde kept for at least 1 w and 5 μm-thick paraffin sections prepared. Immunohistochemical analysis was done by the Avidin-Biotin-Complex (ABC) method. After deparaffinization and quenching of endogenous peroxidase activity by immersion in 3% hydrogen peroxide solution for 5 min, the sections were placed in sodium citrate buffer then immersed in phosphate-buffered saline. Next they were incubated overnight at 4° C. in a moist chamber with the first antibody of interest diluted 1:100 in phosphate-buffered saline containing 1% bovine serum albumin. The reaction product was made visible with 3,3'-diaminobenzidine and viewed under a microscope. For the control specimen, pre-immune serum was used as the first antibody.

Figure 7:
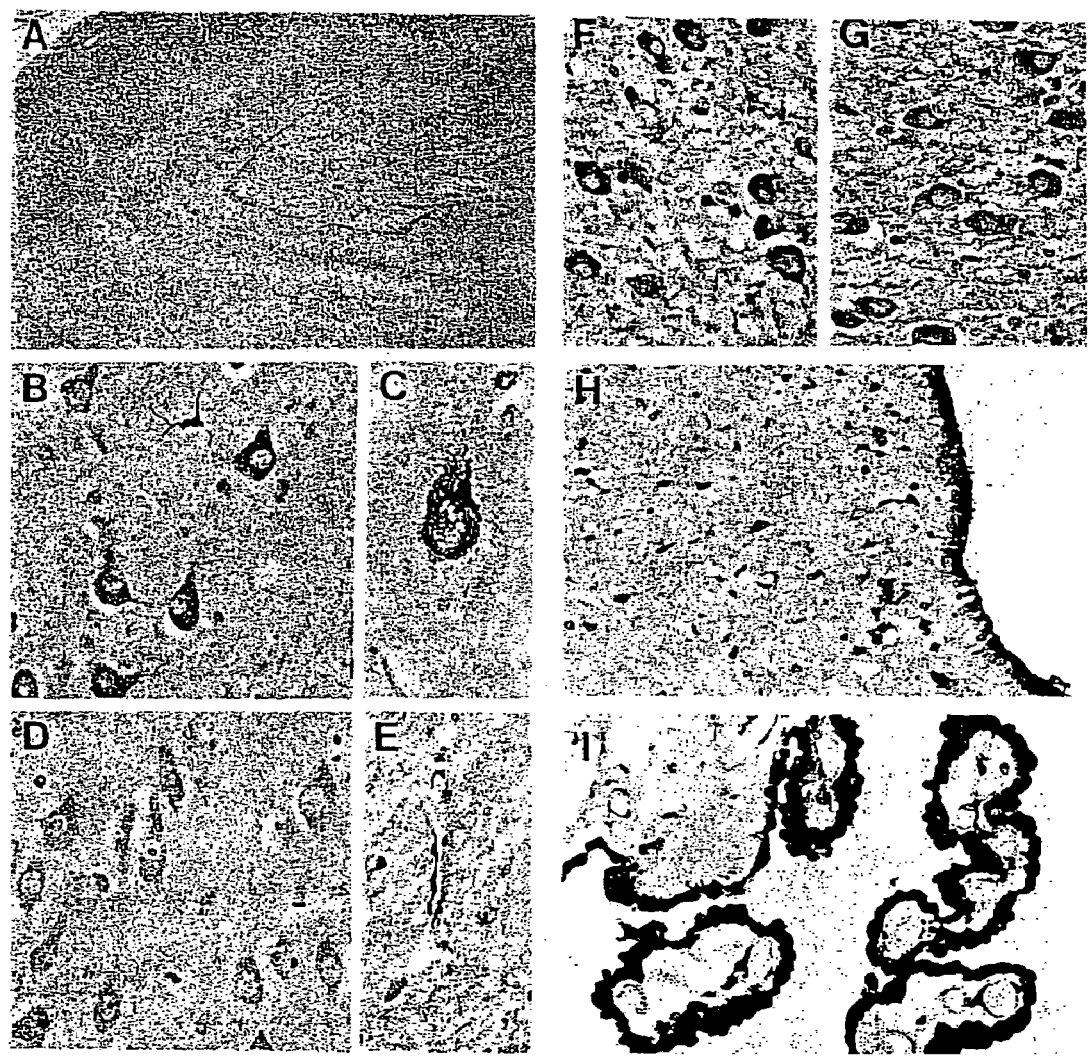
FIG. 7 shows immunohistochemical analysis of normal human brain sections. The antibody used was anti prepro-HBCPB (A, B, C, F and I) or anti C14 (D, E, G and H) antibody. (A), general view of the hippocampus. All pyramidal neurons show immunoreactivity. Magnification×5. (B), pyramidal neurons and activated microglia in the parenchyma of the hippocampus show cytosol immunoreactivities. Magnification×400. (C), activated microglia attached to a pyramidal neuron. Magnification×600. (D), perikarya of the pyramidal neurons show granular anti C14 immunoreactivity. Magnification×400. (E), activated microglia located perivascularly in the lateral geniculate body. Magnification×400. (F) and (G), lateral geniculate body neurons show anti prepro-HBCPB (F) and anti C14 (G) immunoreactivities. Magnification×400. (H), anti C14 immunoreactivity in cytosols of ependymal cells. Magnification×200. (I),anti prepro-HBCPB immunoreactivity in cytosol of choroid plexus cells. Magnification×200.

In all five normal brains, both anti prepro-HBCPB and anti C14 immunoreactivities were detected in the cytosol (perikaryon) of the majority of neurons examined (FIG. 7). The pyramidal neuron of the hippocampus (FIGS. 7A, B, C and D) and the lateral geniculate body neuron (FIGS. 7E, F and G), in particular, are uniformly immunoreactive for these antibodies. Other neurons, such as the hippoglossal motor neuron, thalamic neuron and basal ganglia, also are immunoreactive, but the granular cells of the hippocampus are not stained by these antibodies. The expression of HBCPB confined to the perikaryon is granular and ubiquitous, and anti C14 immunoreactivity also is expressed as granules (FIGS. 7D and G). A portion of the microglia in the parenchyma of the hippocampus, identified by staining with anti human CD68 antibody, intensely expresses both the anti HBCPB and anti C14 immunoreactivities. These microglia are in the extracellular matrix (FIG. 7B) directly adjacent to neurons (FIG. 7C) or are in a perivascular location (FIG. 7E). The present analysis of all the normal brains, using anti glial fibrillary acidic protein (GFAP) antibody, found no GFAP-positive astrocytes that co-express anti prepro-HBCPB and anti C14 immunoreactivities. Other types of cells which distinctively express the HBCPB protease are ependymal and choroid plexus cells (FIGS. 7H and I), in which the ubiquitous expression in the cytosol is granular.

Figure 8:
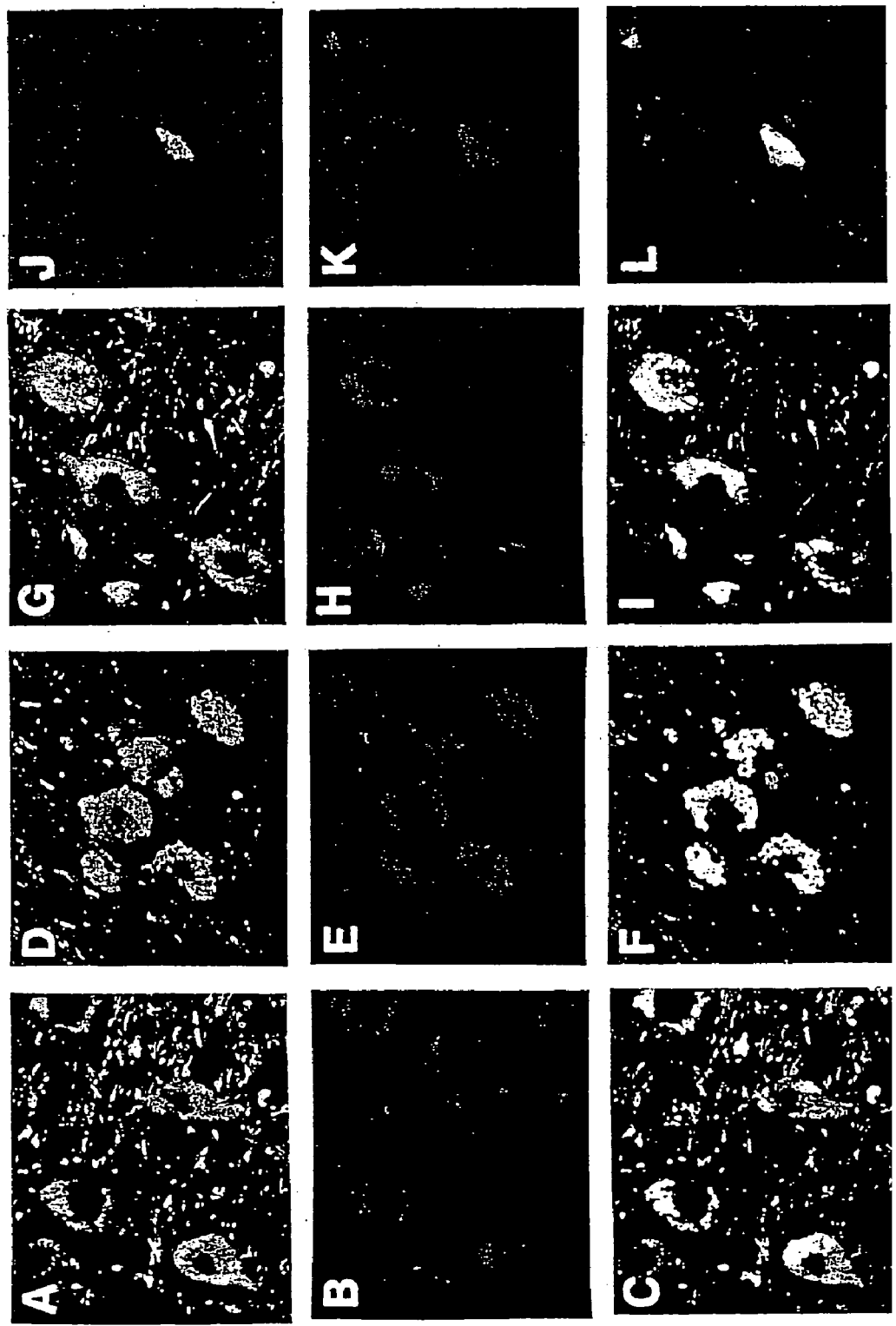
FIG. 8 shows immunofluorescent confocal laser microscopy. Brain sections of pyramidal neurons of the hippocampus (A, B, C, G, H, I, J, K and L) and lateral geniculate body neurons (D, E and F) were double-stained in combination with anti neurofilament antibody (FITC, green) and anti prepro-HBCPB antibody (texas red, red) (A, B, C, G, H and I); with anti neurofilament antibody (FITC) and anti C14 antibody (texas red) (D, E and F); or with anti Aβ 1/40 antibody (FITC) and anti C14 antibody (texas red) (J, K and L). Photomicrographs in C, F, I and L show merged images (yellow) of the two immunoreactivities. Magnification: ×200 (for J, K and L), ×400 (except for J, K and L).

Immunofluorescent confocal laser microscopy was used to determine the precise intracellular neuronal localization of the protease (FIG. 8). Antibodies used were anti human neurofilament antibody (Sanbio, USA), anti human CD68 monoclonal antibody (R&D Systems, USA), anti human GFAP monoclonal antibody (Advance Immunochemical, USA), anti Aβ 1/40 antibody (US Peptides, USA), anti prepro-HBCPB antibody and anti C14 antibody. An MRC-1024 confocal laser microscope (Bio Rad, USA) was used for observation. The immunoreactivity definitely is localized in the cytosol (perikaryon) of both hippocampal pyramidal neurons (FIGS. 8A, B, C, G, H and I) and lateral geniculate body neurons (FIGS. 8D, E and F) in typical granular fashion and is detected by both the anti HBCPB (FIG. 8A through F) and anti C14 (FIG. 8G through I) antibodies. The hippocampal section was also analyzed using the anti human Aβ 1/40 and anti C14 antibodies to analyze the relationship of Aβ peptides and the protease localizations (FIGS. 8J, K and L). These two immunoreactivities are colocalized as granules in the perikarya of pyramidal neurons. C14 immunoreactivity also is present in the glia, possibly in the microglia, whereas Aβ 1/40 immunoreactivity mainly is present in neuronal perikarya.

Figure 9:
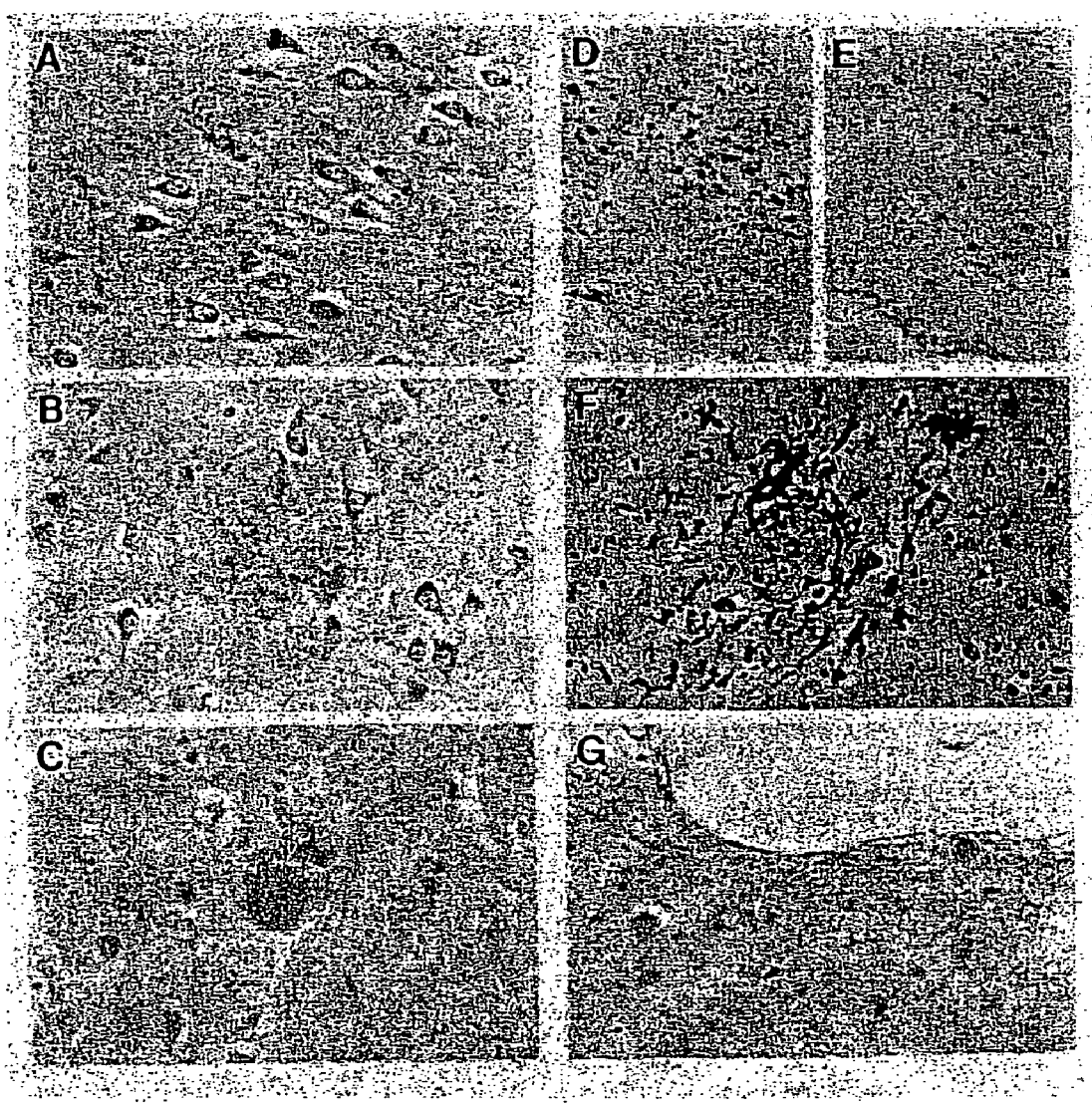
FIG. 9 shows immunohistochemical analysis of brain sections from sporadic Alzheimer's disease patients. (A), pyramidal neurons of the hippocampus. Some neurons show decreased anti prepro-HBCPB immunoreactivities. Magnification×400. (B and C), extracellular deposition of anti C14 immunoreactivity associated with (B) or without (C) glial infiltration in the hippocampus. Magnification×400. (D and E), two sequential sections stained with anti CD68 antibody (C) and anti C14 antibody (D). A portion of the CD68-positive microglia in the hippocampus also express anti C14 immunoreactivity. Magnification×200. (F), a cluster of activated microglia show anti prepro-HBCPB immunoreactivity in the hippocampus. Magnification×200. (G), amyloid bodies do not express anti C14 immunoreactivity. Magnification×200.

The present inventors analyzed brain tissue from five patients with sporadic AD. In AD neurons, especially the hippocampal pyramidal neurons, HBCPB is not ubiquitous as in normal samples, and a portion of the pyramidal neuron shows no immunoreactivity (FIGS. 9A and B). Extracellular deposition of anti C14 immunoreactivity, which appeared as mottled deposition with glial infiltration (FIG. 9B) or more homogeneous deposition without cellular infiltration (FIG. 9C) was detected in parenchyma of the hippocampus in all AD brains examined. In comparison to normal brains, in AD brains the number of microglia harboring immunoreactivity to anti prepro-HBCPB and anti C14 antibodies is enhanced, appearing as a cluster of immunoreactive cells in the hippocampal parenchyma (FIG. 9F). Sequential sections analyzed using anti CD68 antibody which specifically recognizes microglia or with anti C14 antibody showed the immunoreactive cells were microglia, in which both immunoreactivities are colocalized (FIGS. 9D and E). Senile plaque is present in the hippocampus in all the AD cases examined, and anti C14 immunoreactivity is co-localized in a portion of senile plaque as shown in FIG. 9B. Amyloid bodies were detected in all the AD brain tissues, but they did not express immunoreactivity for anti C14 (FIG. 9G). The immunoreactivities of the ependymal and choroid plexus cells in the AD brains were the same as in normal brains.

EXAMPLE 6

Comparison with Known CPB Family Proteins

Since the first purification and characterization of CPB (Folk, J. E. and Gladner, J. A. (1958) J. Biol. Chem., 231, 379-393), CPB has only been clearly identified in the pancreas (Pascual, R. et al. (1989) Eur. J. Biochem., 179, 606-616; Yamamoto, K. K. et al.(1992) J. Biol. Chem., 267, 2575-2581). This protease formerly was regarded as a digestive enzyme secreted only from digestive organs. Relatively recently, CPB or its homologous enzyme has been found in non-digestive tissues such as mast cell secretory granules (Goldstein, S. M. et al. (1989) J. Clin. Invest., 83, 1630-1636; Reynolds, D. S. et al. (1992) J. Clin. Invest., 89, 273-282) and in plasma (Eaton, D. L. et al. (1991) J. Biol. Chem., 266, 21833-21838). On the basis of the well characterized CPs in the pancreas, this group of enzymes exists in two forms of prepro-CP which generate mature enzymes with different characteristics and specificities; the A (CPA) and the B (CPB) forms (Blackburn, S. (1976) Carboxypeptidase A and carboxypeptidase B. In Blackburn, S. (ed.), Enzyme Structure and Function, Marcel Dekker, New York, pp. 169-223). Trypsin activates both CPA and CPB by removing their signal and activation peptides. The biochemical characteristics of CPs in human mast cell secretory granules are similar to those of tissue-type CPs: These 33 to 40 kDa Zn-metallopeptidases are active at a neutral to mild basic pH, are inhibited by potato carboxypeptidase inhibitor, EDTA, phenanthroline and 8-hydroxyquinoline, and are released from mast cells by immunological challenge (Goldstein, S. M. et al. (1989) J. Clin. Invest., 83, 1630-1636).

Structural analysis of prepro-HBCPB-cDNA indicates that HBCPB has a high homology with HPCPB (more than 70%) and moderate homology (approximately 25%) with human mast cell human pancreatic CPBs. In the activation domain, three postulated glycosylation sites for asparagine-linked oligosaccharides are conserved in HBCPB, as in human plasma and mast cell CPBs (FIG. 3). Of these CPBs, the amino acid residues responsible for substrate binding (Arg-183, -Asn-204, Arg-205, Arg-220, Ser-274, Tyr-275, Tyr-326 and Asp-333) and those responsible for zinc binding (His-181, Glu-184 and His-273) are well-conserved. Although the genomic DNA structures that correspond to these two cDNAs have yet to be determined, a comparison of the cDNA structures suggests that the gene for HPCPB is ancestral to that for HBCPB. In view of there being a homologous gene encoding human pancreatic prepro-CPB (Reynolds, D. S. et al. (1992) J. Clin. Invest., 89, 273-282), the exon-intron boundaries of prepro-HBCPB-cDNA can be presumed: The DNA sequence corresponding to the 37 amino acids that is not expressed in the brain protease (HBCPB) is encoded by one exon, corresponding to exon 7 of the human pancreatic gene, the result of a possible alternative splicing mechanism. The 18 amino-acid peptide located in the C-terminal part of prepro-HPCPB, but absent in HBCPB, is not exclusively encoded by one exon. The 52 bp deletion that corresponds to nucleotides 1190 to 1241 of prepro-HPCPB-mRNA resulted in the removal of 18 amino acid residues from HPCPB (385 to 401 amino acid residues) and a frame-shift in HBCPB, generating the 14

C-terminal amino acid residues unique to HBCPB. These findings suggest that prepro-HBCPB-mRNA is not a tissue-specific isoform derived from alternative RNA splicing, rather it is a distinct molecule recently evolved from the same ancestral gene of prepro-HPCPB.

Mature forms of CPs are, in general, highly basic with an overall +10 to 20 positive net charge [(Lys+Arg)−(Asp+Glu)] at neutral pH. Structural analysis showed the mild basic nature of HBCPB, +7 positive net charges; whereas, both HPCPB synthesized in liver and mast cell CPBs have highly basic natures, +11 to 16 positive net charges. These structural characteristics indicate that HBCPB also is a member of the basic CPB family, and therefore has specificities for C-terminal arginine and lysine residues.

In the case of HPCPB, the postulated function is antifibrinolytic activity during clotting, which retards plasma clot lysis by eliminating the plasminogen-binding sites on partially degraded fibrin (Sakharov, D. V. et al. (1997) J. Biol. Chem., 272, 14477-14482). In addition, a comparison of the structures of the C-terminal portions of the brain, plasma and pancreatic CPBs indicated that the 18 amino acid residues, with the most C-terminal residue (glutamic acid at the 385th residue of prepro-HPCPB) for substrate binding lack HBCPB. The C-terminal 14 amino acid residues unique to HBCPB have no homology to any portion of the other CPs identified (FIG. 4B). The peptide(s) with the highest homology to this sequence is located in the N-terminal adjacent to the light-dependent regulation domain of plant chloroplast ATP synthase γ-subunits from various sources (FIG. 4B). ATP synthase catalyzed the synthesis of ATP coupled with an electrochemical gradient of protons produced by the photoelectron transfer chain. Its γ-subunit, which is encoded by the nuclear rather than the chloroplast genome, is believed to be essential in the light-dependent regulation of ATP synthase (Inohara, N. et al. (1991) J. Biol. Chem., 266, 7333-7338). The significance of the unique expression of the C-terminal 14 amino-acid peptides (C14) in HBCPB has yet to be clarified, but the homology to the important domain of ATP synthase suggests a relationship with the 26S proteasome is comprised of ATP-dependent proteases and a variety of proteins assembled in association with ATP.

Pancreatic CPs exist not only as monomers but as binary or ternary complexes with one or two protease(s) that differ in their proteolytic properties (Kerfeleck, B. et al. (1985) Eur. J. Biochem., 151, 515-519). For example, human pancreatic pro-CPA is a binary complex with proproteinase E in the secretory granules (Pascual, R. et al. (1989) Eur. J. Biochem., 179, 606-616). The protease in cattle pancreas is a ternary complex with chymotrypsinogen C/proproteinase E (Kobayashi, R. et al. (1981) J. Biol. Chem., 256, 2460-2465), and that in whale pancreas is a binary complex with chymotrypsinogen C (Yoneda, T. (1980) Comp. Biochem. Physiol. 67B, 81-86). Formation of the complexes of these proteases with complementary proteolytic specificities indicates a function for efficient digestive action. The present inventors presume that the endoproteolytic activity of HBCPB is not owing to a proteinase activity complex with HBCPB, because throughout the preparation of HBCPB both proproteinase E and chymotrypsinogen C differ from HBCPB in terms of molecular mass and affinity in ion-exchange chromatography. The final proteolytic activity product is a single 40 kDa band made visible by sensitive silver staining. Furthermore, the inventors did not used SDS, which induces autolysis of human proteinase E (Sziegoleit, A. et al. (1985) Eur. J. Biochem., 151, 595-599), in the preparation process, which proteinase would have been detected if it was co-purified with HBCPB.

The difference in the efficiency of proteolysis when natural APP or APP pretreated with chondroitinase was used suggests that the charge effect interferes with proteolysis. HBCPB with moderate positive charges may preferentially more efficiently trap the natural APP that has negatively charged chondroitin sulfate moieties than it does those without them. If this is so in human brain, there are a variety of molecules belonging to APP family. A portion of brain APP has as a component the unique proteoglycan, appican (Shioi, J. et al. (1992) J. Biol. Chem., 267, 13819-13822). Its core protein is the APP695 lacking 18 amino acid residues encoded by exon 15, and it carries chondroitin sulfate glycoconjugates bound to the recognition signal for glucosaminoglycan binding that is generated in the amino acid residues between exons 14 and 16 (Pangalos et al. 1995, J. Biol. Chem., 270, 10388-10391). In the step of immunoprecipitating natural brain APP using anti cAPP antibody, APLP1 and APLP2 which share homologous sequences with APP may be co-precipitated; in fact, chondroitin sulfate is bound to a particular isoform of APLP2 as it is in APP (Thinakaran, G. et al. (1995) J. Biol. Chem., 270, 16522-16525). When, however, anti Aβ 1/14 antibody was used in the analysis, no fragments derived from APLP1 and APLP2 were detected because those proteins have no sequence homologous to the extracellular domains of Aβ (Wasco, W. et al. (1992) Proc. Natl. Acad. Sci. USA, 89, 10758-10762; Sprecher, C. A. et al. (1993) Biochemistry, 32, 4481-4486). The Aβ-bearing peptides derived from APP and/or proteoglycans with isoforms of APP, including appican and as yet unidentified isoforms, therefore are targets for HBCPB. The molecular diversity of brain APP also seems to be associated with a strict substrate-protease relationship,.giving rise to the tissue- and species-specificities of AD pathophysiology.

EXAMPLE 7

Proteolytic Function as a Carboxypeptidase

When human brain carboxypeptidase B (from 0.01 pM to 0.2 pM) was applied at 37° C. for 16 hours using synthetic Aβ 1-40 and Aβ 1-42 (0.1 pM each) as substrates, low-molecular weight peptides formed in a dose-dependent manner. In Western blot analysis, low-molecular weight peptides (in which several amino acids have shifted) can be confirmed by anti-Aβ-N-terminus antibody regarding the Aβ 1-40 substrate, however this cannot be confirmed by the anti-Aβ 40 fragment antibody. On the other hand, low-molecular weight peptides (in which several amino acids have shifted) can be confirmed by anti-Aβ-N-terminus antibody regarding the Aβ 1-42 substrate, however this cannot be confirmed by the anti-Aβ 42 fragment antibody. These experimental facts suggest the possibility that human brain carboxypeptidase B degrades the C-terminal amino acid of Aβ peptide in the neuron, and especially, has the physiological function of metabolizing the highly cohesive Aβ 1-42 to convert it to the less toxic Aβ peptide.

EXAMPLE 8

Expression of Human Brain CPB in Neuroectoderm-derived Cells

Immunohistochemical analysis using antibodies against human brain CPB (antibodies against the 14 C-terminal amino acids: anti-C14 module antibody) on tissue sections of pancreas and testis derived from humans and rats showed marked immunostaining in the cytoplasm of Langerhans' islet β-cells (insulin-producing cells), and in the cytoplasm of testis interstitium Leydig's cells (FIG. 10) for both species.

These results suggest that human brain CPB has the function of metabolizing amylin, which, similar to insulin, is produced in the β-cells and has β-amyloid-like properties. When the function of amylin is considered in the context of insulin action, human brain CPB may possibly be related to the pathological physiology of a specific type of diabetes.

Additionally, expression of human brain CPB was confirmed in the cytoplasm of human testis Leydig's cells. Therefore, human brain CPB may possibly be involved in the production, secretion, degradation, and such, of many proteinous hormones produced in these endocrine cells.

INDUSTRIAL APPLICABILITY

The brain CPB protein of the present invention has the biological activity to cleave brain APP to produce Aβ-containing peptides. In addition, it has the biological activity to degrade Aβ peptide from the C terminus. Therefore, brain CPB protein may be a therapeutic drug that regulates pathological APP metabolisms and production of Aβ-containing peptides, and in addition, is a useful tool for elucidating the molecular mechanism of Aβ peptide production and the onset of diseases relating to Aβ peptide production (for example, Alzheimer's disease) Furthermore, brain CPB expressed in trace amounts in the spinal fluid and even in the peripheral blood is useful as a marker for CNS diseases to test and diagnose abnormalities in APP and Aβ metabolisms. In addition, brain CPB may be used to screen candidate compounds for drugs for diseases that cause Aβ accumulation in the brain. That is, the present invention has provided a novel and effective method for preventing, treating, and testing diseases that cause Aβ accumulation in the brain.

SEQUENCE LISTING

```
<160> NUMBER OF SEQ ID NOS: 9

<210> SEQ ID NO 1
<211> LENGTH: 1573
<212> TYPE: DNA
<213> ORGANISM: Homo sapiens
<220> FEATURE:
<221> NAME/KEY: CDS
<222> LOCATION: (18)..(1097)

<400> SEQUENCE: 1
agaaaattgc tgttggg atg aag ctt tgc agc ctt gca gtc ctt gta ccc          50
                   Met Lys Leu Cys Ser Leu Ala Val Leu Val Pro
                    1               5                  10 att gtt ctc ttc tgt gag cag cat gtc ttc gcg ttc cag agt ggc caa         98
Ile Val Leu Phe Cys Glu Gln His Val Phe Ala Phe Gln Ser Gly Gln
             15                  20                  25 gtt cta gct gct ctt cct aga acc tct agg caa gtt caa gtt cta cag        146
Val Leu Ala Ala Leu Pro Arg Thr Ser Arg Gln Val Gln Val Leu Gln
         30                  35                  40 aat ctt act aca aca tat gag att gtt ctc tgg cag ccg gta aca gct        194
Asn Leu Thr Thr Thr Tyr Glu Ile Val Leu Trp Gln Pro Val Thr Ala
     45                  50                  55 gac ctt att gtg aag aaa aaa caa gtc cat ttt ttt gta aat gca tct        242
Asp Leu Ile Val Lys Lys Lys Gln Val His Phe Phe Val Asn Ala Ser
 60                  65                  70                  75 gat gtc gac aat gtg aaa gcc cat tta aat gtg agc gga att cca tgc        290
Asp Val Asp Asn Val Lys Ala His Leu Asn Val Ser Gly Ile Pro Cys
                 80                  85                  90 agt gtc ttg ctg gca gac gtg gaa gat ctt att caa cag cag att tcc        338
Ser Val Leu Leu Ala Asp Val Glu Asp Leu Ile Gln Gln Gln Ile Ser
             95                 100                 105 aac gac aca gtc agc ccc cga gcc tcc gca tcg tac tat gaa cag tat        386
Asn Asp Thr Val Ser Pro Arg Ala Ser Ala Ser Tyr Tyr Glu Gln Tyr
        110                 115                 120 cac tca cta aat gaa atc tat tct tgg ata gaa ttt ata act gag agg        434
His Ser Leu Asn Glu Ile Tyr Ser Trp Ile Glu Phe Ile Thr Glu Arg
    125                 130                 135 cat cct gat atg ctt aca aaa atc cac att gga tcc tca ttt gag aag        482
His Pro Asp Met Leu Thr Lys Ile His Ile Gly Ser Ser Phe Glu Lys
140                 145                 150                 155 tac cca ctc tat gtt tta aag gtt tct gga aaa gaa caa aca gcc aaa        530
```

```
                Tyr Pro Leu Tyr Val Leu Lys Val Ser Gly Lys Glu Gln Thr Ala Lys
                            160                 165                 170 aat gcc ata tgg att gac tgt gga atc cat gcc aga gaa tgg atc tct       578
Asn Ala Ile Trp Ile Asp Cys Gly Ile His Ala Arg Glu Trp Ile Ser
            175                 180                 185 cct gct ttc tgc ttg tgg ttc ata ggc cat aat cga atg tgg aga aag       626
Pro Ala Phe Cys Leu Trp Phe Ile Gly His Asn Arg Met Trp Arg Lys
            190                 195                 200 aac cgt tct ttc tat gcg aac aat cat tgc atc gga aca gac ctg aat       674
Asn Arg Ser Phe Tyr Ala Asn Asn His Cys Ile Gly Thr Asp Leu Asn
        205                 210                 215 agc aac ttt gtc tcc aaa cac tgg tgt gag gaa ggt gca tcc agt tcc       722
Ser Asn Phe Val Ser Lys His Trp Cys Glu Glu Gly Ala Ser Ser Ser
220                 225                 230                 235 tca tgc tcg gaa acc tac tgt gga ctt tat cct gag tca gaa cca gaa       770
Ser Cys Ser Glu Thr Tyr Cys Gly Leu Tyr Pro Glu Ser Glu Pro Glu
                240                 245                 250 gtg aag gca gtg gct agt ttc ttg aga aga aat atc aac cag att aaa       818
Val Lys Ala Val Ala Ser Phe Leu Arg Arg Asn Ile Asn Gln Ile Lys
                    255                 260                 265 gca tac atc agc atg cat tca tac tcc cag cat ata gtg ttt cca tat       866
Ala Tyr Ile Ser Met His Ser Tyr Ser Gln His Ile Val Phe Pro Tyr
                270                 275                 280 tcc tat aca cga agt aaa agc aaa gac cat gag gaa ctg tct cta gta       914
Ser Tyr Thr Arg Ser Lys Ser Lys Asp His Glu Glu Leu Ser Leu Val
        285                 290                 295 gcc agt gaa gca gtt cgt gct att gac aaa act agt aaa aat acc agg       962
Ala Ser Glu Ala Val Arg Ala Ile Asp Lys Thr Ser Lys Asn Thr Arg
300                 305                 310                 315 tat aca cat ggc cat ggc tca gaa acc tta tac cta gct cct gga ggt      1010
Tyr Thr His Gly His Gly Ser Glu Thr Leu Tyr Leu Ala Pro Gly Gly
                320                 325                 330 ggg gac gat tgg atc tat gat ttg ggc atc aaa tat tcg ttt aca tca      1058
Gly Asp Asp Trp Ile Tyr Asp Leu Gly Ile Lys Tyr Ser Phe Thr Ser
                    335                 340                 345 aac cca cct gta gag aag ctt ttg ccg ctg tct cta aaa tagcttggca       1107
Asn Pro Pro Val Glu Lys Leu Leu Pro Leu Ser Leu Lys
            350                 355                 360 tgtcattagg aatgtttaat gcccctgatt ttatcattct gcttccgtat tttaatttac    1167
tgattccagc aagaccaaat cattgtatca gattatttttt aagtttatc cgtagttttg    1227 ataaaagatt ttcctattcc ttggttctgt cagagaacct aataagtgct actttgccat    1287
taaggcagac tagggttcat gtcttttttac cctttaaaaa aaaattgtaa aagtctagtt   1347
acctactttt tctttgattt tcgacgtttg actagccatc tcaagcaact ttcgacgttt    1407
gactagccat ctcaagcaag tttaatcaaa gatcatctca cgctgatcat tggatcctac    1467
tcaacaaaag gaagggtggt cagaagtaca ttaaagattt ctgctccaaa ttttcaataa    1527
atttcttctt ctcctttaaa aaaaaaaaaa aaaaaaaaaa aaaaa                    1573

<210> SEQ ID NO 2
<211> LENGTH: 360
<212> TYPE: PRT
<213> ORGANISM: Homo sapiens

<400> SEQUENCE: 2

Met Lys Leu Cys Ser Leu Ala Val Leu Val Pro Ile Val Leu Phe Cys
 1                5                  10                  15

Glu Gln His Val Phe Ala Phe Gln Ser Gly Gln Val Leu Ala Ala Leu
```

```
                        20                  25                  30

Pro Arg Thr Ser Arg Gln Val Gln Val Leu Gln Asn Leu Thr Thr Thr
            35                  40                  45

Tyr Glu Ile Val Leu Trp Gln Pro Val Thr Ala Asp Leu Ile Val Lys
50                  55                  60

Lys Lys Gln Val His Phe Phe Val Asn Ala Ser Asp Val Asp Asn Val
65                  70                  75                  80

Lys Ala His Leu Asn Val Ser Gly Ile Pro Cys Ser Val Leu Leu Ala
                85                  90                  95

Asp Val Glu Asp Leu Ile Gln Gln Gln Ile Ser Asn Asp Thr Val Ser
            100                 105                 110

Pro Arg Ala Ser Ala Ser Tyr Tyr Glu Gln Tyr His Ser Leu Asn Glu
        115                 120                 125

Ile Tyr Ser Trp Ile Glu Phe Ile Thr Glu Arg His Pro Asp Met Leu
    130                 135                 140

Thr Lys Ile His Ile Gly Ser Ser Phe Glu Lys Tyr Pro Leu Tyr Val
145                 150                 155                 160

Leu Lys Val Ser Gly Lys Glu Gln Thr Ala Lys Asn Ala Ile Trp Ile
                165                 170                 175

Asp Cys Gly Ile His Ala Arg Glu Trp Ile Ser Pro Ala Phe Cys Leu
            180                 185                 190

Trp Phe Ile Gly His Asn Arg Met Trp Arg Lys Asn Arg Ser Phe Tyr
        195                 200                 205

Ala Asn Asn His Cys Ile Gly Thr Asp Leu Asn Ser Asn Phe Val Ser
    210                 215                 220

Lys His Trp Cys Glu Glu Gly Ala Ser Ser Ser Cys Ser Glu Thr
225                 230                 235                 240

Tyr Cys Gly Leu Tyr Pro Glu Ser Glu Pro Glu Val Lys Ala Val Ala
                245                 250                 255

Ser Phe Leu Arg Arg Asn Ile Asn Gln Ile Lys Ala Tyr Ile Ser Met
            260                 265                 270

His Ser Tyr Ser Gln His Ile Val Phe Pro Tyr Ser Tyr Thr Arg Ser
        275                 280                 285

Lys Ser Lys Asp His Glu Glu Leu Ser Leu Val Ala Ser Glu Ala Val
    290                 295                 300

Arg Ala Ile Asp Lys Thr Ser Lys Asn Thr Arg Tyr Thr His Gly His
305                 310                 315                 320

Gly Ser Glu Thr Leu Tyr Leu Ala Pro Gly Gly Asp Asp Trp Ile
                325                 330                 335

Tyr Asp Leu Gly Ile Lys Tyr Ser Phe Thr Ser Asn Pro Pro Val Glu
            340                 345                 350

Lys Leu Leu Pro Leu Ser Leu Lys
        355                 360

<210> SEQ ID NO 3
<211> LENGTH: 338
<212> TYPE: PRT
<213> ORGANISM: Homo sapiens

<400> SEQUENCE: 3

Phe Gln Ser Gly Gln Val Leu Ala Ala Leu Pro Arg Thr Ser Arg Gln
1               5                   10                  15

Val Gln Val Leu Gln Asn Leu Thr Thr Thr Tyr Glu Ile Val Leu Trp
                20                  25                  30
```

```
Gln Pro Val Thr Ala Asp Leu Ile Val Lys Lys Gln Val His Phe
             35                  40                  45

Phe Val Asn Ala Ser Asp Val Asp Asn Val Lys Ala His Leu Asn Val
 50                  55                  60

Ser Gly Ile Pro Cys Ser Val Leu Leu Ala Asp Val Glu Asp Leu Ile
 65                  70                  75                  80

Gln Gln Gln Ile Ser Asn Asp Thr Val Ser Pro Arg Ala Ser Ala Ser
                 85                  90                  95

Tyr Tyr Glu Gln Tyr His Ser Leu Asn Glu Ile Tyr Ser Trp Ile Glu
            100                 105                 110

Phe Ile Thr Glu Arg His Pro Asp Met Leu Thr Lys Ile His Ile Gly
            115                 120                 125

Ser Ser Phe Glu Lys Tyr Pro Leu Tyr Val Leu Lys Val Ser Gly Lys
        130                 135                 140

Glu Gln Thr Ala Lys Asn Ala Ile Trp Ile Asp Cys Gly Ile His Ala
145                 150                 155                 160

Arg Glu Trp Ile Ser Pro Ala Phe Cys Leu Trp Phe Ile Gly His Asn
                165                 170                 175

Arg Met Trp Arg Lys Asn Arg Ser Phe Tyr Ala Asn Asn His Cys Ile
            180                 185                 190

Gly Thr Asp Leu Asn Arg Asn Phe Ala Ser Lys His Trp Cys Glu Glu
        195                 200                 205

Gly Ala Ser Ser Ser Ser Cys Ser Glu Thr Tyr Cys Gly Leu Tyr Pro
210                 215                 220

Glu Ser Glu Pro Glu Val Lys Ala Val Ala Ser Phe Leu Arg Arg Asn
225                 230                 235                 240

Ile Asn Gln Ile Lys Ala Tyr Ile Ser Met His Ser Tyr Ser Gln His
                245                 250                 255

Ile Val Phe Pro Tyr Ser Tyr Thr Arg Ser Lys Ser Lys Asp His Glu
            260                 265                 270

Glu Leu Ser Leu Val Ala Ser Glu Ala Val Arg Ala Ile Glu Lys Thr
        275                 280                 285

Ser Lys Asn Thr Arg Tyr Thr His Gly His Gly Ser Glu Thr Leu Tyr
    290                 295                 300

Leu Ala Pro Gly Gly Gly Asp Asp Trp Ile Tyr Asp Leu Gly Ile Lys
305                 310                 315                 320

Tyr Ser Phe Thr Ser Asn Pro Pro Val Glu Lys Leu Pro Leu Ser
                325                 330                 335

Leu Lys

<210> SEQ ID NO 4
<211> LENGTH: 246
<212> TYPE: PRT
<213> ORGANISM: Homo sapiens

<400> SEQUENCE: 4

Ala Ser Ala Ser Tyr Tyr Glu Gln Tyr His Ser Leu Asn Glu Ile Tyr
 1               5                  10                  15

Ser Trp Ile Glu Phe Ile Thr Glu Arg His Pro Asp Met Leu Thr Lys
             20                  25                  30

Ile His Ile Gly Ser Ser Phe Glu Lys Tyr Pro Leu Tyr Val Leu Lys
         35                  40                  45

Val Ser Gly Lys Glu Gln Thr Ala Lys Asn Ala Ile Trp Ile Asp Cys
 50                  55                  60
```

-continued

```
Gly Ile His Ala Arg Glu Trp Ile Ser Pro Ala Phe Cys Leu Trp Phe
 65                  70                  75                  80

Ile Gly His Asn Arg Met Trp Arg Lys Asn Arg Ser Phe Tyr Ala Asn
             85                  90                  95

Asn His Cys Ile Gly Thr Asp Leu Asn Arg Asn Phe Ala Ser Lys His
        100                 105                 110

Trp Cys Glu Glu Gly Ala Ser Ser Ser Cys Ser Glu Thr Tyr Cys
    115                 120                 125

Gly Leu Tyr Pro Glu Ser Glu Pro Glu Val Lys Ala Val Ala Ser Phe
    130                 135                 140

Leu Arg Arg Asn Ile Asn Gln Ile Lys Ala Tyr Ile Ser Met His Ser
145                 150                 155                 160

Tyr Ser Gln His Ile Val Phe Pro Tyr Ser Tyr Thr Arg Ser Lys Ser
                165                 170                 175

Lys Asp His Glu Glu Leu Ser Leu Val Ala Ser Glu Ala Val Arg Ala
            180                 185                 190

Ile Glu Lys Thr Ser Lys Asn Thr Arg Tyr Thr His Gly His Gly Ser
        195                 200                 205

Glu Thr Leu Tyr Leu Ala Pro Gly Gly Asp Asp Trp Ile Tyr Asp
    210                 215                 220

Leu Gly Ile Lys Tyr Ser Phe Thr Ser Asn Pro Val Glu Lys Leu
225                 230                 235                 240

Leu Pro Leu Ser Leu Lys
                245

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence:
      Artificially synthesized oligopeptide sequence

<400> SEQUENCE: 5

Thr Pro Glu Glu Arg His Leu Ser Lys Met Gln Gln Asn Gly Tyr Glu
  1               5                  10                  15

Asn Pro Thr Tyr Lys Phe Phe Glu
            20

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 6
gcctccgcat cgtactatga acagtatcac                                    30

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 7
ggttcatagg ccataatcga atgt                                          24
```

```
<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 8 tcagggcat taaacattcc taat                                            24

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence:
      Artificially synthesized oligopeptide sequence

<400> SEQUENCE: 9

Ser Asn Pro Pro Val Glu Lys Leu Leu Pro Leu Ser Leu Lys
  1               5                  10
```

The invention claimed is:

1. An isolated antibody that binds to human brain carboxypeptidase B consisting of SEQ ID NO:9.

2. The antibody of claim 1 which is a monoclonal antibody or a polyclonal antibody.

3. A reagent comprising the antibody of claim 2.

4. A reagent comprising the antibody of claim 1.

5. A method for detecting human brain carboxypeptidase B protein, comprising the steps of:

(a) preparing a sample from a subject, (b) contacting the sample with the antibody of claim 1, and (c) detecting human brain carboxypeptidase B protein contained within the sample by measuring antibody binding, thereby determining the presence of the human brain carboxypeptidase B protein.

6. The method of claim 5, wherein said sample is spinal fluid or serum.

* * * * *

UNITED STATES PATENT AND TRADEMARK OFFICE
CERTIFICATE OF CORRECTION

| | |
|---|---|
| PATENT NO. | : 7,524,934 B2 |
| APPLICATION NO. | : 11/233958 |
| DATED | : April 28, 2009 |
| INVENTOR(S) | : Matsumoto |

It is certified that error appears in the above-identified patent and that said Letters Patent is hereby corrected as shown below:

Delete sequence listing at column 27 line 20 - column 37 line 34
Please add the attached sequence listing in its place.

Signed and Sealed this
Twelfth Day of July, 2011

David J. Kappos
*Director of the United States Patent and Trademark Office*

CERTIFICATE OF CORRECTION (continued)
U.S. Pat. No. 7,524,934 B2

In the Sequence Listing:

SEQUENCE LISTING

<110> AKIRA MATSUMOTO

<120> Human Brain Carboxypeptidase B

<130> 082371-000010US

<140> US 11/233,958
<141> 2005-09-22

<150> PCT/JP00/02878
<151> 2005-09-22

<150> US 09/980,881
<151> 2002-03-28

<150> JP 1999-125169
<151> 1999-04-30

<160> 12

<170> PatentIn Ver. 2.0

<210> 1
<211> 1573
<212> DNA
<213> Homo sapiens

<220>
<221> CDS
<222> (18)..(1097)

<400> 1

```
agaaaattgc tgttggg atg aag ctt tgc agc ctt gca gtc ctt gta ccc      50
                   Met Lys Leu Cys Ser Leu Ala Val Leu Val Pro
                    1               5                      10 att gtt ctc ttc tgt gag cag cat gtc ttc gcg ttc cag agt ggc caa      98
Ile Val Leu Phe Cys Glu Gln His Val Phe Ala Phe Gln Ser Gly Gln
             15                  20                  25 gtt cta gct gct ctt cct aga acc tct agg caa gtt caa gtt cta cag     146
Val Leu Ala Ala Leu Pro Arg Thr Ser Arg Gln Val Gln Val Leu Gln
         30                  35                  40 aat ctt act aca aca tat gag att gtt ctc tgg cag ccg gta aca gct     194
Asn Leu Thr Thr Thr Tyr Glu Ile Val Leu Trp Gln Pro Val Thr Ala
     45                  50                  55 gac ctt att gtg aag aaa aaa caa gtc cat ttt ttt gta aat gca tct     242
Asp Leu Ile Val Lys Lys Lys Gln Val His Phe Phe Val Asn Ala Ser
 60                  65                  70                  75 gat gtc gac aat gtg aaa gcc cat tta aat gtg agc gga att cca tgc     290
Asp Val Asp Asn Val Lys Ala His Leu Asn Val Ser Gly Ile Pro Cys
                 80                  85                  90 agt gtc ttg ctg gca gac gtg gaa gat ctt att caa cag cag att tcc     338
Ser Val Leu Leu Ala Asp Val Glu Asp Leu Ile Gln Gln Gln Ile Ser
             95                 100                 105 aac gac aca gtc agc ccc cga gcc tcc gca tcg tac tat gaa cag tat     386
Asn Asp Thr Val Ser Pro Arg Ala Ser Ala Ser Tyr Tyr Glu Gln Tyr
        110                 115                 120
```

```
cac tca cta aat gaa atc tat tct tgg ata gaa ttt ata act gag agg   434
His Ser Leu Asn Glu Ile Tyr Ser Trp Ile Glu Phe Ile Thr Glu Arg
    125                 130                 135 cat cct gat atg ctt aca aaa atc cac att gga tcc tca ttt gag aag   482
His Pro Asp Met Leu Thr Lys Ile His Ile Gly Ser Ser Phe Glu Lys
140                 145                 150                 155 tac cca ctc tat gtt tta aag gtt tct gga aaa gaa caa aca gcc aaa   530
Tyr Pro Leu Tyr Val Leu Lys Val Ser Gly Lys Glu Gln Thr Ala Lys
                160                 165                 170 aat gcc ata tgg att gac tgt gga atc cat gcc aga gaa tgg atc tct   578
Asn Ala Ile Trp Ile Asp Cys Gly Ile His Ala Arg Glu Trp Ile Ser
            175                 180                 185 cct gct ttc tgc ttg tgg ttc ata ggc cat aat cga atg tgg aga aag   626
Pro Ala Phe Cys Leu Trp Phe Ile Gly His Asn Arg Met Trp Arg Lys
        190                 195                 200 aac cgt tct ttc tat gcg aac aat cat tgc atc gga aca gac ctg aat   674
Asn Arg Ser Phe Tyr Ala Asn Asn His Cys Ile Gly Thr Asp Leu Asn
    205                 210                 215 agc aac ttt gtc tcc aaa cac tgg tgt gag gaa ggt gca tcc agt tcc   722
Ser Asn Phe Val Ser Lys His Trp Cys Glu Glu Gly Ala Ser Ser Ser
220                 225                 230                 235 tca tgc tcg gaa acc tac tgt gga ctt tat cct gag tca gaa cca gaa   770
Ser Cys Ser Glu Thr Tyr Cys Gly Leu Tyr Pro Glu Ser Glu Pro Glu
                240                 245                 250 gtg aag gca gtg gct agt ttc ttg aga aga aat atc aac cag att aaa   818
Val Lys Ala Val Ala Ser Phe Leu Arg Arg Asn Ile Asn Gln Ile Lys
            255                 260                 265 gca tac atc agc atg cat tca tac tcc cag cat ata gtg ttt cca tat   866
Ala Tyr Ile Ser Met His Ser Tyr Ser Gln His Ile Val Phe Pro Tyr
        270                 275                 280 tcc tat aca cga agt aaa agc aaa gac cat gag gaa ctg tct cta gta   914
Ser Tyr Thr Arg Ser Lys Ser Lys Asp His Glu Glu Leu Ser Leu Val
    285                 290                 295 gcc agt gaa gca gtt cgt gct att gac aaa act agt aaa aat acc agg   962
Ala Ser Glu Ala Val Arg Ala Ile Asp Lys Thr Ser Lys Asn Thr Arg
300                 305                 310                 315 tat aca cat ggc cat ggc tca gaa acc tta tac cta gct cct gga ggt  1010
Tyr Thr His Gly His Gly Ser Glu Thr Leu Tyr Leu Ala Pro Gly Gly
                320                 325                 330 ggg gac gat tgg atc tat gat ttg ggc atc aaa tat tcg ttt aca tca  1058
Gly Asp Asp Trp Ile Tyr Asp Leu Gly Ile Lys Tyr Ser Phe Thr Ser
            335                 340                 345 aac cca cct gta gag aag ctt ttg ccg ctg tct cta aaa tagcttggca   1107
Asn Pro Pro Val Glu Lys Leu Leu Pro Leu Ser Leu Lys
        350                 355                 360 tgtcattagg aatgtttaat gcccctgatt ttatcattct gcttccgtat tttaatttac 1167 tgattccagc aagaccaaat cattgtatca gattattttt aagttttatc cgtagttttg 1227 ataaaagatt ttcctattcc ttggttctgt cagagaacct aataagtgct actttgccat 1287
```

CERTIFICATE OF CORRECTION (continued)
U.S. Pat. No. 7,524,934 B2

Page 4 of 10

```
taaggcagac tagggttcat gtcttttac cctttaaaaa aaaattgtaa aagtctagtt 1347
acctactttt tctttgattt tcgacgtttg actagccatc tcaagcaact ttcgacgttt 1407
gactagccat ctcaagcaag tttaatcaaa gatcatctca cgctgatcat tggatcctac 1467
tcaacaaaag gaagggtggt cagaagtaca ttaaagattt ctgctccaaa ttttcaataa 1527
atttcttctt ctcctttaaa aaaaaaaaaa aaaaaaaaaa aaaaaa                1573
```

<210> 2
<211> 360
<212> PRT
<213> Homo sapiens

<400> 2

| Met | Lys | Leu | Cys | Ser | Leu | Ala | Val | Leu | Val | Pro | Ile | Val | Leu | Phe | Cys |
|---|---|---|---|---|---|---|---|---|---|---|---|---|---|---|---|
| 1 | | | | 5 | | | | | 10 | | | | | 15 | |
| Glu | Gln | His | Val | Phe | Ala | Phe | Gln | Ser | Gly | Gln | Val | Leu | Ala | Ala | Leu |
| | | | 20 | | | | | 25 | | | | | 30 | | |
| Pro | Arg | Thr | Ser | Arg | Gln | Val | Gln | Val | Leu | Gln | Asn | Leu | Thr | Thr | Thr |
| | | 35 | | | | | 40 | | | | | 45 | | | |
| Tyr | Glu | Ile | Val | Leu | Trp | Gln | Pro | Val | Thr | Ala | Asp | Leu | Ile | Val | Lys |
| | 50 | | | | | 55 | | | | | 60 | | | | |
| Lys | Lys | Gln | Val | His | Phe | Phe | Val | Asn | Ala | Ser | Asp | Val | Asp | Asn | Val |
| 65 | | | | | 70 | | | | | 75 | | | | | 80 |
| Lys | Ala | His | Leu | Asn | Val | Ser | Gly | Ile | Pro | Cys | Ser | Val | Leu | Leu | Ala |
| | | | | 85 | | | | | 90 | | | | | 95 | |
| Asp | Val | Glu | Asp | Leu | Ile | Gln | Gln | Gln | Ile | Ser | Asn | Asp | Thr | Val | Ser |
| | | | 100 | | | | | 105 | | | | | 110 | | |
| Pro | Arg | Ala | Ser | Ala | Ser | Tyr | Tyr | Glu | Gln | Tyr | His | Ser | Leu | Asn | Glu |
| | | 115 | | | | | 120 | | | | | 125 | | | |
| Ile | Tyr | Ser | Trp | Ile | Glu | Phe | Ile | Thr | Glu | Arg | His | Pro | Asp | Met | Leu |
| | 130 | | | | | 135 | | | | | 140 | | | | |
| Thr | Lys | Ile | His | Ile | Gly | Ser | Ser | Phe | Glu | Lys | Tyr | Pro | Leu | Tyr | Val |
| 145 | | | | | 150 | | | | | 155 | | | | | 160 |
| Leu | Lys | Val | Ser | Gly | Lys | Glu | Gln | Thr | Ala | Lys | Asn | Ala | Ile | Trp | Ile |
| | | | | 165 | | | | | 170 | | | | | 175 | |
| Asp | Cys | Gly | Ile | His | Ala | Arg | Glu | Trp | Ile | Ser | Pro | Ala | Phe | Cys | Leu |
| | | | 180 | | | | | 185 | | | | | 190 | | |
| Trp | Phe | Ile | Gly | His | Asn | Arg | Met | Trp | Arg | Lys | Asn | Arg | Ser | Phe | Tyr |
| | | 195 | | | | | 200 | | | | | 205 | | | |
| Ala | Asn | Asn | His | Cys | Ile | Gly | Thr | Asp | Leu | Asn | Ser | Asn | Phe | Val | Ser |
| | 210 | | | | | 215 | | | | | 220 | | | | |
| Lys | His | Trp | Cys | Glu | Glu | Gly | Ala | Ser | Ser | Ser | Cys | Ser | Glu | Thr |
| 225 | | | | | 230 | | | | | 235 | | | | | 240 |
| Tyr | Cys | Gly | Leu | Tyr | Pro | Glu | Ser | Glu | Pro | Glu | Val | Lys | Ala | Val | Ala |
| | | | | 245 | | | | | 250 | | | | | 255 | |

```
        Ser Phe Leu Arg Arg Asn Ile Asn Gln Ile Lys Ala Tyr Ile Ser Met
                    260                 265                 270

His Ser Tyr Ser Gln His Ile Val Phe Pro Tyr Ser Tyr Thr Arg Ser
                275                 280                 285

Lys Ser Lys Asp His Glu Glu Leu Ser Leu Val Ala Ser Glu Ala Val
                290                 295                 300

Arg Ala Ile Asp Lys Thr Ser Lys Asn Thr Arg Tyr Thr His Gly His
        305                 310                 315                 320

Gly Ser Glu Thr Leu Tyr Leu Ala Pro Gly Gly Asp Asp Trp Ile
                        325                 330                 335

Tyr Asp Leu Gly Ile Lys Tyr Ser Phe Thr Ser Asn Pro Pro Val Glu
                        340                 345                 350

Lys Leu Leu Pro Leu Ser Leu Lys
                    355                 360

<210> 3
<211> 338
<212> PRT
<213> Homo sapiens

<400> 3
Phe Gln Ser Gly Gln Val Leu Ala Ala Leu Pro Arg Thr Ser Arg Gln
1               5                   10                  15

Val Gln Val Leu Gln Asn Leu Thr Thr Thr Tyr Glu Ile Val Leu Trp
            20                  25                  30
```

```
Gln Pro Val Thr Ala Asp Leu Ile Val Lys Lys Lys Gln Val His Phe
        35                  40                  45
Phe Val Asn Ala Ser Asp Val Asp Asn Val Lys Ala His Leu Asn Val
    50                  55                  60
Ser Gly Ile Pro Cys Ser Val Leu Leu Ala Asp Val Glu Asp Leu Ile
65                  70                  75                  80
Gln Gln Gln Ile Ser Asn Asp Thr Val Ser Pro Arg Ala Ser Ala Ser
                85                  90                  95
Tyr Tyr Glu Gln Tyr His Ser Leu Asn Glu Ile Tyr Ser Trp Ile Glu
            100                 105                 110
Phe Ile Thr Glu Arg His Pro Asp Met Leu Thr Lys Ile His Ile Gly
        115                 120                 125
Ser Ser Phe Glu Lys Tyr Pro Leu Tyr Val Leu Lys Val Ser Gly Lys
    130                 135                 140
Glu Gln Thr Ala Lys Asn Ala Ile Trp Ile Asp Cys Gly Ile His Ala
145                 150                 155                 160
Arg Glu Trp Ile Ser Pro Ala Phe Cys Leu Trp Phe Ile Gly His Asn
            165                 170                 175
Arg Met Trp Arg Lys Asn Arg Ser Phe Tyr Ala Asn Asn His Cys Ile
        180                 185                 190
Gly Thr Asp Leu Asn Arg Asn Phe Ala Ser Lys His Trp Cys Glu Glu
        195                 200                 205
```

```
Gly Ala Ser Ser Ser Ser Cys Ser Glu Thr Tyr Cys Gly Leu Tyr Pro
    210             215                 220

Glu Ser Glu Pro Glu Val Lys Ala Val Ala Ser Phe Leu Arg Arg Asn
225             230             235                         240

Ile Asn Gln Ile Lys Ala Tyr Ile Ser Met His Ser Tyr Ser Gln His
                245             250                 255

Ile Val Phe Pro Tyr Ser Tyr Thr Arg Ser Lys Ser Lys Asp His Glu
            260             265             270

Glu Leu Ser Leu Val Ala Ser Glu Ala Val Arg Ala Ile Glu Lys Thr
        275             280             285

Ser Lys Asn Thr Arg Tyr Thr His Gly His Gly Ser Glu Thr Leu Tyr
    290             295             300

Leu Ala Pro Gly Gly Gly Asp Asp Trp Ile Tyr Asp Leu Gly Ile Lys
305             310             315                         320

Tyr Ser Phe Thr Ser Asn Pro Pro Val Glu Lys Leu Leu Pro Leu Ser
            325             330                 335

Leu Lys
```

<210> 4
<211> 246
<212> PRT
<213> Homo sapiens

```
<400> 4
Ala Ser Ala Ser Tyr Tyr Glu Gln Tyr His Ser Leu Asn Glu Ile Tyr
 1               5                  10                  15

Ser Trp Ile Glu Phe Ile Thr Glu Arg His Pro Asp Met Leu Thr Lys
            20                  25                  30

Ile His Ile Gly Ser Ser Phe Glu Lys Tyr Pro Leu Tyr Val Leu Lys
        35                  40                  45

Val Ser Gly Lys Glu Gln Thr Ala Lys Asn Ala Ile Trp Ile Asp Cys
    50                  55                  60

Gly Ile His Ala Arg Glu Trp Ile Ser Pro Ala Phe Cys Leu Trp Phe
65                  70                  75                  80

Ile Gly His Asn Arg Met Trp Arg Lys Asn Arg Ser Phe Tyr Ala Asn
                85                  90                  95

Asn His Cys Ile Gly Thr Asp Leu Asn Arg Asn Phe Ala Ser Lys His
            100                 105                 110

Trp Cys Glu Glu Gly Ala Ser Ser Ser Cys Ser Glu Thr Tyr Cys
        115                 120                 125

Gly Leu Tyr Pro Glu Ser Glu Pro Glu Val Lys Ala Val Ala Ser Phe
130                 135                 140

Leu Arg Arg Asn Ile Asn Gln Ile Lys Ala Tyr Ile Ser Met His Ser
145                 150                 155                 160

Tyr Ser Gln His Ile Val Phe Pro Tyr Ser Tyr Thr Arg Ser Lys Ser
            165                 170                 175
```

```
        Lys Asp His Glu Glu Leu Ser Leu Val Ala Ser Glu Ala Val Arg Ala
                    180                 185                 190

Ile Glu Lys Thr Ser Lys Asn Thr Arg Tyr Thr His Gly His Gly Ser
                    195                 200                 205

Glu Thr Leu Tyr Leu Ala Pro Gly Gly Gly Asp Asp Trp Ile Tyr Asp
                    210                 215                 220

Leu Gly Ile Lys Tyr Ser Phe Thr Ser Asn Pro Pro Val Glu Lys Leu
        225                 230                 235                 240

Leu Pro Leu Ser Leu Lys
                        245

<210> 5
<211> 24
<212> PRT
<213> Artificial Sequence

<220>
<223> Description of Artificial Sequence: Artificially
      synthesized oligopeptide sequence <400> 5
Thr Pro Glu Glu Arg His Leu Ser Lys Met Gln Gln Asn Gly Tyr Glu
 1               5                  10                  15

Asn Pro Thr Tyr Lys Phe Phe Glu
            20

<210> 6
<211> 30
<212> DNA
<213> Artificial Sequence

<220>
<223> Description of Artificial Sequence: Artificially
      synthesized primer sequence <400> 6
gcctccgcat cgtactatga acagtatcac                                      30

<210> 7
<211> 24
<212> DNA
<213> Artificial Sequence

<220>
<223> Description of Artificial Sequence: Artificially
      synthesized primer sequence <400> 7
ggttcatagg ccataatcga atgt                                            24

<210> 8
<211> 24
<212> DNA
<213> Artificial Sequence
```

```
<220>
<223> Description of Artificial Sequence: Artificially
      synthesized primer sequence <400> 8
tcagggggcat taaacattcc taat                                    24

<210> 9
<211> 14
<212> PRT
<213> Artificial Sequence

<220>
<223> Description of Artificial Sequence: Artificially
      synthesized oligopeptide sequence <400> 9
Ser Asn Pro Pro Val Glu Lys Leu Leu Pro Leu Ser Leu Lys
 1               5                  10

<210> 10
<211> 14
<212> PRT
<213> Artificial Sequence

<220>
<223> Description of Artificial Sequence: Artificially
      synthesized oligopeptide sequence <400> 10
Ser Asn Pro Thr Ile Gly Thr Leu Leu Pro Leu Ser Pro Met
 1               5                  10

<210> 11
<211> 14
<212> PRT
<213> Artificial Sequence

<220>
<223> Description of Artificial Sequence: Artificially
      synthesized oligopeptide sequence <400> 11
Ser Asp Pro Val Ile His Thr Leu Leu Pro Leu Ser Pro Lys
 1               5                  10

<210> 12
<211> 14
<212> PRT
<213> Artificial Sequence

<220>
<223> Description of Artificial Sequence: Artificially
      synthesized oligopeptide sequence <400> 12
Ser Glu Pro Val Ile His Thr Leu Leu Pro Leu Ser Pro Lys
 1               5                  10
```